United States Patent
Salamone et al.

(10) Patent No.: US 10,688,159 B2
(45) Date of Patent: Jun. 23, 2020

(54) COMPOSITIONS AND KITS FOR TREATING PRURITUS AND METHODS OF USING THE SAME

(71) Applicant: ROCHAL INDUSTRIES, LLC, San Antonio, TX (US)

(72) Inventors: Joseph Charles Salamone, San Antonio, TX (US); Ann Beal Salamone, San Antonio, TX (US); Kelly Xiaoyu Chen Leung, San Antonio, TX (US); Katelyn Elizabeth Reilly, San Antonio, TX (US)

(73) Assignee: ROCHAL INDUSTRIES, LLC, San Antonio, TX (US)

( * ) Notice: Subject to any disclaimer, the term of this patent is extended or adjusted under 35 U.S.C. 154(b) by 0 days.

(21) Appl. No.: 15/078,719

(22) Filed: Mar. 23, 2016

(65) Prior Publication Data

US 2016/0199459 A1  Jul. 14, 2016

Related U.S. Application Data

(62) Division of application No. 14/511,988, filed on Oct. 10, 2014, now abandoned.

(51) Int. Cl.

| | | |
|---|---|---|
| A61K 38/47 | (2006.01) | |
| A61K 9/00 | (2006.01) | |
| A61K 31/785 | (2006.01) | |
| A61K 9/70 | (2006.01) | |
| A61K 9/107 | (2006.01) | |
| A61K 47/02 | (2006.01) | |
| A61K 47/38 | (2006.01) | |
| A61K 47/18 | (2017.01) | |
| A61K 47/24 | (2006.01) | |
| A61K 38/46 | (2006.01) | |
| A61K 47/06 | (2006.01) | |
| A61K 47/10 | (2017.01) | |
| A61K 9/08 | (2006.01) | |
| A61K 38/54 | (2006.01) | |
| A61K 31/155 | (2006.01) | |

(52) U.S. Cl.
CPC ............ *A61K 38/47* (2013.01); *A61K 9/0014* (2013.01); *A61K 9/08* (2013.01); *A61K 9/1075* (2013.01); *A61K 9/7007* (2013.01); *A61K 31/155* (2013.01); *A61K 31/785* (2013.01); *A61K 38/465* (2013.01); *A61K 38/54* (2013.01); *A61K 47/02* (2013.01); *A61K 47/06* (2013.01); *A61K 47/10* (2013.01); *A61K 47/18* (2013.01); *A61K 47/24* (2013.01); *A61K 47/38* (2013.01); *C12Y 301/01003* (2013.01); *C12Y 301/01* (2013.01); *C12Y 302/01001* (2013.01); *C12Y 302/01002* (2013.01); *C12Y 302/01003* (2013.01); *C12Y 304/24003* (2013.01)

(58) Field of Classification Search
None
See application file for complete search history.

(56) References Cited

U.S. PATENT DOCUMENTS

| | | | |
|---|---|---|---|
| 2,120,667 A | 6/1938 | Gruskin | |
| 2,917,433 A | 12/1959 | Goldman | |
| 3,003,917 A | 10/1961 | Beiler | |
| 3,409,719 A | 11/1968 | Noe | |
| 4,668,228 A | 5/1987 | Bolton | |
| 4,717,737 A | 1/1988 | Kern | |
| 4,719,235 A | 1/1988 | Kern | |
| 4,772,465 A | 9/1988 | Collins | |
| 4,885,310 A | 12/1989 | Kern | |
| 5,120,656 A | 6/1992 | O'Leary | |
| 5,206,026 A | 4/1993 | Sharik | |
| 5,543,149 A | 8/1996 | Rubin | |
| 5,670,142 A | 9/1997 | Rubin | |
| 6,548,556 B2 | 4/2003 | Hobson | |
| 7,368,128 B2 | 5/2008 | Qvist | |
| 8,119,124 B2 | 2/2012 | Gorecki | |
| 8,486,664 B2 | 7/2013 | Keller | |
| 8,540,983 B2 | 9/2013 | Gorecki | |
| 8,754,045 B2 | 6/2014 | Livingston | |
| 2002/0114798 A1 | 8/2002 | Hobson | |
| 2004/0076671 A1 | 4/2004 | Tippett | |
| 2004/0081681 A1* | 4/2004 | Vromen | A61K 8/9794 424/449 |
| 2004/0105874 A1 | 6/2004 | Batt | |
| 2007/0237812 A1 | 10/2007 | Patel et al. | |
| 2008/0044459 A1 | 2/2008 | Livingston | |

(Continued)

FOREIGN PATENT DOCUMENTS

| | | |
|---|---|---|
| CN | 102973927 | 3/2013 |
| EP | 0456467 | 11/1991 |

(Continued)

OTHER PUBLICATIONS

Paul et al. (2013) Advances in Skin and Wound Care 26(7): 320-332 (Year: 2013).*
Advanced Tissue (2014) Understanding Wound Healing and the Itching Dilemma (https://advancedtissue.com/2014/10/understanding-wound-healing-itching-dilemma/) (Year: 2014).*
Lerner, E. (2018) Wounds 30(1): 1-3 (Year: 2018).*
Paul, J. (2013) Ostomy Wound Management 59(7): 28-34 (Year: 2013).*

(Continued)

*Primary Examiner* — Robert J Yamasaki
(74) *Attorney, Agent, or Firm* — Duane Morris LLP; Jason M. Nolan; Gregory M. Lefkowitz (57) ABSTRACT

A treatment for pruritus is described that is based upon amylase. The amylases (α-, β-, γ-amylase) are noted for the cleavage of the α-glycosidic bonds of polysaccharides, yielding lower molecular weight carbohydrate/sugar fragments. It has now been found that α-amylase is effective in the reduction of pruritus (itching) of affected tissue.

21 Claims, 2 Drawing Sheets

(56) References Cited

U.S. PATENT DOCUMENTS

| | | |
|---|---|---|
| 2010/0135919 A1 | 6/2010 | Barron |
| 2012/0104047 A1 | 5/2012 | Lim |
| 2013/0202581 A1 | 8/2013 | Fallon |
| 2013/0273026 A1 | 10/2013 | Gavini |
| 2013/0287859 A1 | 10/2013 | Balaguer et al. |
| 2015/0086529 A1 | 3/2015 | Hillenbrand |

FOREIGN PATENT DOCUMENTS

| | | |
|---|---|---|
| RU | 2407512 | 12/2010 |
| WO | 1984/002846 | 8/1984 |
| WO | 1999/046368 | 9/1999 |
| WO | 2007/144856 | 12/2007 |
| WO | 2008/063229 | 5/2008 |
| WO | 2010/004367 | 1/2010 |
| WO | 2012/013646 | 2/2012 |
| WO | 2012/155027 | 11/2012 |
| WO | 2013016255 | 1/2013 |

OTHER PUBLICATIONS

Parnell, LKS (2018) Wounds 30(1): 17-36 (Year: 2018).*
Elmariah et al., "Topical Therapies for Pruritus", Seminars in Cutaneous Medicine and Surgery, vol. 30, No. 2, 2011, pp. 118-126.

\* cited by examiner

COMPOSITIONS AND KITS FOR TREATING PRURITUS AND METHODS OF USING THE SAME

CROSS-REFERENCE TO RELATED APPLICATIONS

This application is a divisional application of U.S. patent application Ser. No. 14/511,988 filed Oct. 10, 2014, the entirety of which is incorporated herein by reference.

FIELD OF THE INVENTION

This invention relates generally to the treatment, amelioration, and prevention of pruritus and its potential concomitant irritation and inflammation in humans and animals using α-amylase and formulations thereof.

BACKGROUND OF THE INVENTION

Pruritus is a condition that involves localized or general itching, which often leads to the urge to scratch and the stimulation of sensory nerve endings. Scratching can be severe, resulting in irritation and inflammation of the skin, as well as bleeding and infection. Although pruritus usually occurs in the skin, it can also occur in non-cutaneous sites, such as mucous membranes or the cornea. A variety of causes of pruritus are recognized, including external and exogenous effects, localized skin disorders, and systemic diseases. Wound healing after injury or surgery is often accompanied by localized itching. Pruritus can also be a component of inflammation.

Histamine is one of the most important mediators of itch, although other chemical substances have also been implicated, such as neuropeptides that act by releasing histamine from mast cells, and itching caused by them responds to antihistamines. Other substances act independently; therefore, antihistamines are not effective in some forms of pruritus.

A wide variety of treatment modalities for pruritus are reported, including nonspecific topical agents such as emollients and counter-irritants, topical drugs such as corticosteroids, agonists, such as cannabinoids or calcineurin inhibitors, local anesthetics, and antihistamines, anticonvulsants, antidepressants, and micro-opioid receptor antagonists, as well as by physical modalities, such as UV-based phototherapy, cooling, transcutaneous electrical nerve stimulation, and acupuncture. Some of these treatments are effective in pruritic conditions of a particular etiology, while others may show general but nonspecific benefit.

Other anti-pruritic and wound-healing agents reported for the treatment of skin disorders have involved the use of topically applied proteolytic enzyme compositions. In U.S. Pat. No. 3,003,917, compositions useful for the acceleration of wound healing include relaxin, a proteolytic enzyme or enzymes, and an amylolytic enzyme or enzymes. Relaxin is a protein hormone and is in the insulin family. The proteolytic enzymes which may be used in this formulation are trypsin, chymotrypsin, pepsin, papain, bromelain, ficin and mixtures of proteolytic enzymes obtained from bacteria. The amylolytic enzymes which may be used are mixtures of bacterial amylases, pancreatic or α-amylase and β-amylase. A particularly effective composition for accelerating wound healing comprises relaxin, trypsin, and pancreatic amylase, in respective weight ratios of 5:1:1.

In International Patent Publication Number WO 1984/002846, a topical ointment for skin surface wounds is described that includes wound-healing amounts papain, bromelain, trypsin, chymotrypsin, pancreatin, lipase, amylase, aloe extract and an organic astringent agent formulated in a carrier mixture of penetrating and non-penetrating emollient oils and a polyhydric alcohol emollient, with a plurality of protease. The ointment is reported to reduce inflammation at the site of skin-surface wounds and acts to enhance the normal anti-inflammatory activities of the body.

In International Patent Publication Number WO 2010/004367, the use of a mixture of superoxide dismutase and catalase enzymes for treating pruritus and alleviating its symptoms is reported.

In International Patent Number WO 8402846, a topical ointment for skin surface wounds comprising wound-healing amounts of papain, bromelain, trypsin, chymotrypsin, pancreatin, lipase, amylase, aloe extract and an organic astringent agent formulated in a carrier mixture of penetrating and non-penetrating emollient oils and a polyhydric alcohol emollient is reported. The ointment reportedly reduces inflammation at the site of skin-surface wounds and acts to enhance the normal anti-inflammatory activities of the body, particularly by enhancing the normal anti-inflammatory activity of proteolytic enzymes. The compositions utilized preferably include wound-cleansing amounts of topically-applied pancreatic digestive enzymes such as lipases and/or amylases, which are considered to affect the fats and carbohydrates contained in the structure of bacteria and viruses, wherein many types of viruses possess an outer cell envelope composed of protein, lipid and carbohydrate constituents. According to the WO'846 publication, amylase and/or lipase, in conjunction with the proteolytic enzymes, are thought to act synergistically to degrade the cell-envelope and protein and lipid components of the virus particle so as to inactivate the pathogenicity of viruses contained in or entering the wound. In this manner, wound-healing is purported to be aided by the control of infectious microorganisms.

In International Patent Publication Number WO 1999/046368, a method for treating wounds comprising the step of administering an effective amount of a carbohydrate-active enzyme is discussed that reportedly has broad-specificity for debriding burns and other wounds. According to the WO'368 publication, because of the high concentrations of glycosaminoglycans (GAGs) in skin, for burn patients, enzymes that degrade glycosaminoglycans are considered to be useful adjuncts to burn wound debridement. GAGs are sugar chains consisting of repeating polymers of acidic polysaccharides, composed of building blocks of the following sugars in various combinations: galactose, glucose, N-acetylglucosamine, N-acetylgalactosamine, glucuronic acid, galacturonic acid and iduronic acid. It is known that carbohydrates have important roles in the functioning of living organisms. In addition to their metabolic roles, carbohydrates are structural components of the human body, being covalently attached to numerous other entities such as proteins (i.e., as glycoproteins). Human skin is reported to contain 10% by weight of GAGs, which include heparin, heparan sulfate, chondroitin sulfate, hyaluronic acid (hyaluronan), dermatan sulfate, and keratan sulfate, with chondroitin sulfate being the most prevalent glycosaminoglycan. Chondroitin sulfate has β-1,3- and β-1,4-linkages between predominant monomeric units. In the WO'368 publication, the term "carbohydrate-active enzyme" is used to specifically encompass carbohydrate reducing enzymes, where examples of such enzymes include glycosaminoglycan reducing enzymes such as hyaluronidases, chondroitinases, dermatanases, heparanases, heparinases and keratanases, with preferred carbohydrate-active enzymes of chondroitinases and hyaluronidases.

In U.S. Patent Application 2013/0273026, a method for modulating inflammatory molecules with amylase, by modulating Immunoglobulin E (IgE) antibody mediated histamine release from an IgE receptor positive cell has been reported. The method is reportedly capable of releasing histamine in vitro or in vivo, wherein an effective dose of an amylase peptide or a derivative thereof is provided to the IgE receptor positive cell in vitro or in vivo under conditions that would permit binding of amylase to free IgE in solution to form an IgE-amylase binding pair, thereby inhibiting the binding of free IgE to the IgE receptor positive cell. IgE is described as a protein involved in the upregulation of a chronic inflammatory response (for example, the chronic inflammatory response observed in Type I diabetes). According to one embodiment disclosed in the '026 publication, disrupting the function of IgE with amylase provides an ameliorating effect on chronic inflammation. This process has purported efficacy relative to chronic inflammation in cystic fibrosis, Type I and Type II diabetes, such as by modulating serum insulin, treating obesity, stabilizing serum blood amylase for treating insulin resistance, modulating histamine levels in a mammal, and treating chronic inflammation. The compositions of the '026 publication are reported to be administered systemically, such as orally or by injection, topically, and transdermally.

SUMMARY

The pruritus formulations of this invention contain the enzyme α-amylase. All amylases (α-, β-, γ-amylase) are a family of enzymes that preferentially hydrolyze the α-glycosidic bonds of polysaccharides, yielding lower molecular weight carbohydrate/sugar fragments. α-Amylase is the preferred enzyme of this invention. The benefits of α-amylase include the fact it occurs naturally in humans and other mammals, and it is also is found in plants, bacteria and fungi.

Whereas α-amylases catalyze the hydrolysis of internal α-(1-4)-linkages of glucose polymers as their main reaction, some α-amylases, particularly saccharifying amylases, can catalyze transfer reactions in addition to hydrolysis (U.S. Pat. No. 8,486,664; International Patent Application Number WO 2012/013646). These α-amylases are capable of transferring glycoside residues to low molecular weight alcohols as well as to water, a property related to the transferase activity of the glycosidases. It is not known whether such a transglycosylation process is operative in the reduction of pruritus or inflammation of wounds as related to this invention.

Without wishing to be bound by the theory for amelioration of pruritus, in this investigation a novel method for pruritus amelioration was unexpectedly found, with potential concomitant irritation and inflammation reduction, through the topical application of the enzyme α-amylase, an enzyme primarily noted for the cleavage of α-1,4-glycosidic bonds in starch into low molecular weight sugars. Surprisingly, this effect of pruritus amelioration has not been previously reported although α-amylase has been studied in many formats.

The physical behavior of skin tissue is determined primarily by an extensive extracellular matrix (ECM) composed of an interlocking mesh of fibrous proteins and glycosaminoglycans (GAGs). The GAGs are carbohydrate polymers and are usually attached to ECM proteins, forming proteoglycans. In skin, type I collagen is the main protein component of the ECM and the main proteoglycan components are decorin and versican. Presumably, these core proteins bind to the surface of type I collagen fibrils, which provide mechanical strength to skin. Proteoglycan binding is required for appropriate assembly of collagen fibrils in the ECM and inhibits cleavage of collagen fibrils by matrix metalloproteases. Proteoglycans are composed of a glycoprotein core to which one or several GAG chains are covalently bonded. Four different classes of glycosaminoglycans exist in vertebrates, chondroitin sulfate, dermatan sulfate, keratin sulfate, and heparan sulfate/heparin. Hyaluronan (hyaluronic acid) is one of the chief components of the extracellular matrix, and it contributes significantly to cell proliferation and migration. However, unlike the other glycosaminoglycans, hyaluronan does not attach to proteins to form proteoglycans but binds and retains water molecules and fills the gaps between collagen fibrils.

The GAGs are attached to a serine residue of the core protein by both glycosidic bonds (primarily by chondroitin sulfate, dermatan sulfate) and α-1,4-bonds (primarily by heparan sulfate/heparin), with the predominant GAG being chondroitin sulfate. For internal linkages, hyaluronan and chondroitin sulfate are predominantly composed of β-1,3- and β-1,4-linkages, dermatan sulfate has predominantly α-1,3- and β-1,4-linkages, and heparin/heparan sulfate have a mixture of β-1,4- and α-1,4-linkages, wherein the primary repeating unit does not contain 3 or more α-1,4-linkages (Glycosaminoglycans and Proteoglycans, sigma.com/glycobiology), as required for cleavage by α-amylase.

A previous study discussed a method for treating wounds comprising the step of administering an effective amount of a carbohydrate-active enzyme for treatment of wounds, wherein such enzymes were preferentially chondroitinases, enzymes that catalyze the hydrolysis of the chondroitin chains on proteoglycans containing (1-4)-β-D- and (1-3)-β-D-linkages, and hyaluronidases, enzymes that cleave hyaluronan, which contains β-1,4- and β-1,3-glycosidic bonds, with limited ability to degrade chondroitin and chondroitin sulfates.

This compositions and methods described herein pertain to the use of a non-protease hydrolytic enzyme for treatment of pruritus and its resulting irritation and inflammation, where it was unexpectedly found that α-amylase was able to ameliorate this condition. The amylase family of α-amylase, α-amylase, and γ-amylase are hydrolytic enzymes that aid in the cleavage of bonds in sugar residues in polysaccharides. Of particular interest is α-amylase. It is found in two primary types in the human body: salivary amylase and pancreatic amylase. In saliva, salivary amylase is responsible for the breakdown of starch and glycogen into glucose, maltose, and dextrin. Pancreatic amylase further degrades starches in the digestive system.

In some embodiments, the non-proteolytic component is greater than the proteolytic component of the enzymatic pruritic composition. In some embodiments, a ratio of non-proteolytic enzymes to proteolytic enzymes in the enzymatic pruritic composition is at least 4:1, at least 5:1, or at least 10:1, at least 20:1 at least 40:1, at least 60:1, at least 80:1, or at least 100:1. Where the amount of proteolytic enzymes is 0 and the amount of non-proteolytic enzyme is greater than 0, the ratio is 00:1. In some embodiments, the enzymatic pruritic composition comprises less than 0.01% by weight proteolytic enzymes, or less than 0.001% by weight of proteolytic enzymes, based on the total weight of the debridement composition. In some embodiments, the enzymatic pruritic composition comprises up to 20% by weight of proteolytic enzyme, or up to 15% by weight of proteolytic enzyme, or up to 10% by weight of proteolytic enzyme.

Relative to the three forms of amylase, α-amylase (also called 1,4-α-D-glucan glucanohydrolase) is an endoamylase that is found in all living organisms. It functions in a random manner by a multiple-attack mechanism on starch, glycogen and related polysaccharides and oligosaccharides with α-1,4-glycosidic linkages, ultimately yielding glucose and maltose as well as larger oligosaccharides, none of which are present in human skin. α-Amylase hydrolyzes 1,4-α-D-glucosidic linkages in polysaccharides that contain 3 or more 1,4-α-linked D-glucose units (Sigma Aldrich, http://www.sigmaaldrich.com/life-science/metabolomics/enzyme-explorer/learning-center/carbohydrate-analysis.html). However, α-amylase cannot hydrolyze α-1,6-bonds in glycogen and amylopectin.

β-Amylase (also called 1,4-α-D-glucan maltohydrolase) and γ-amylase (also called (amyloglucosidase, glucan 1,4-α-glucosidase, and glucoamylase) are exoamylases that are found exclusively in plants and microorganisms. Like α-amylase, β-amylase cannot hydrolyze α-1,6-bonds. The β-amylase enzyme acts on the same substrates as α-amylase, but it removes successive maltose units from the non-reducing end. γ-Amylase releases β-D-glucose successively from the non-reducing end of the polysaccharide chains. Various forms of γ-amylase can hydrolyze 1,6-α-D-glucosidic bonds when the next bond in the sequence is a 1,4-bond, and some preparations can hydrolyze 1,6- and 1,3-α-D-glucosidic bonds in other polysaccharides. In a related fashion, isoamylase, an isoenzyme form of amylase, is an enzyme that catalyzes the cleavage of α-1,6-glycosidic branching sections in glycogen, amylopectin, and certain dextrins.

Calcium and chloride ions are essential for the activity of α-amylase. One $Ca^{2+}$ is tightly bound by each enzyme molecule, facilitating the proper conformation for hydrolytic activity, and chloride ions have been regarded as natural activators of the enzyme. Excess calcium stabilizes α-amylase towards heat. It optimum temperature range for catalytic activity is between 40° C. and 45° C. and a pH of 7-7.5.

Amylases (α-, β-, γ-amylase) are a family of enzymes that preferentially hydrolyze the α-glycosidic bonds of polysaccharides, yielding lower molecular weight carbohydrate/sugar fragments. In some embodiments, the compositions and methods described herein include α-amylase as some or all of the amylase. α-Amylase randomly cleaves the 1,4-α-D-glycosidic linkages between the adjacent glucose units in the linear amylose chain of starch. A significant benefit of α-amylase as used herein is that it occurs naturally in humans and other mammals, and it is also found in plants, bacteria and fungi. Microbial amylase is generally preferred for commercial use because it is normally cheaper to produce, its activity is more controllable, and it has reliable supplies of raw materials. Plant and animal sources can contain more harmful material than microbial based amylases, including phenolic compounds (from plants), endogenous enzyme inhibitors, and proteases.

Since amylase is not proteolytic, it does not self-digest in water, and it is more stable compared to proteolytic enzymes under similar aqueous conditions. The high stability of amylase facilitates its storage in a hydrophilic formulation, which can be easily removed from the skin by washing.

Starch molecules are glucose polymers linked together by α-1,4- and α-1,6-glycosidic bonds, consisting of linear amylose and branched amylopectin components. In order to make use of the carbon and energy stored in starch, amylase, as part of the human digestive system, cleaves starch at multiple points, converting starch into smaller sugars, which are eventually converted to glucose units. Because of the existence of two types of linkages, the α-1,4- and the α-1,6-glycosidic bonds, different structures are possible for starch molecules. An unbranched, single chain polymer with only the α-1,4-glucosidic bonds is called amylose. On the other hand, the presence of α-1,6-glucosidic linkages results in the branched glucose polymer of amylopectin. The degree of branching in amylopectin is approximately one per twenty-five glucose units in the unbranched segments. Another closely related compound functioning as the glucose storage in human and animal cells is called glycogen, which has one branching per 12 glucose units. Glycogen has a structure similar to that of amylopectin, except that the branches in glycogen tend to be shorter and more numerous. Neither amylose, nor amylopectin, nor glycogen is believed to be present in human or animal skin as a component of stabilizing or interacting with collagen of the extracellular matrix.

The specificity of the bond attacked by α-amylase depends on the source of the enzyme. Currently, two major classes of α-amylases are commercially produced through microbial fermentation. Based on where cleavage occurs in the glucose polymer chain, the initial step in random depolymerization of starch is the splitting of large chains into various smaller sized segments. The breakdown of large segments drastically reduces the viscosity of the gelatinized starch solution, resulting in liquefaction because of the reduced viscosity of the solution. The final stage of the depolymerization is saccharification, which results predominantly in the formation of monosaccharides, disaccharides, and trisaccharides.

Because bacterial α-amylase randomly attacks only the α-1,4-bonds, it belongs to the liquefying category. On the other hand, the fungal α-amylase belongs to the saccharifying category and attacks the second linkage from the nonreducing terminals (i.e., C4 end) of the straight segment, resulting in the splitting off of two glucose units at a time, giving the disaccharide maltose. The bond breakage is thus more extensive in saccharifying enzymes than in liquefying enzymes. The starch chains are literally chopped into small bits and pieces. Finally, γ-amylase selectively attacks the last bond on the nonreducing terminals and can act on both the α-1,4- and the α-1,6-glucosidic linkages at a relative rate of 1:20, resulting in the splitting off of simple glucose units into the solution. α-Amylase and γ-amylase may be used together to convert starch to simple sugars.

Amylase has also been used in the cleaning of hard surfaces and fabrics, as described in International Patent Publication Number WO 2007/144856, which include all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, laundry bars, mouthwashes, denture cleaners, car or carpet shampoos, bathroom cleaners; hair shampoos and hair rinses; shower gels and foam baths and metal cleaners; as well as cleaning auxiliaries such as bleach additives and "stain-stick" or pre-treat types.

Amylases are one of the main enzymes used in industry. Amylases have potential application in a wide number of industrial processes such as food, fermentation and pharmaceutical industries. Although α-amylases can be obtained from plants, animals and microorganisms, enzymes from fungal and bacterial sources have dominated applications in industry, including microorganisms of *Bacillus* spp. and *Aspergillus* spp., with most commercial amylases being produced from bacterial sources such as *Bacillus licheniformis, Bacillus amyloliquefaciens, Bacillus subtilis*, or *Bacillus stearothermophilus*.

The enzymatic pruritic compositions described herein can be formulated as a liquid, gel, powder, paste, ointment, lotion, slurry, balm, emulsion, or microemulsion, and can be delivered to pruritic tissue with or without irritation and inflammation as a liquid, gel, hydrogel, foam, spray, dressing, mesh, bandage, or film, wherein the latter may contain film-forming polymers, or a non-degradable substrate, such as a dressing, bandage, tape, or foamed material. The enzymatic pruritic compositions can include one or more pharmaceutically or cosmetically acceptable carrier that is compatible with the enzymatic debridement composition. Examples of pharmaceutically or cosmetically acceptable carriers, include, but are not limited to, water, normal saline (isotonic saline), Dulbecco's phosphate-buffered saline (DPBS), phosphate buffered saline (PBS), saline solutions containing added calcium chloride, Ringer's solution, Good buffer solutions, glycerin, propylene glycol, ethanol, isopropanol, butane-1,3-diol, liquid poly(alkylene glycols (e.g., poly(ethylene glycol), methyl ether-terminated poly(ethylene glycol), poly(ethylene glycol-block-propylene glycol-block-ethylene glycol)), polyoxyethylene ethers, and water-soluble liquid silicone polyethers, or water-insoluble media, such as, isopropyl myristate, isopropyl palmitate, mineral oil, dimethicone, fatty alcohols, and petrolatum. In some embodiments, excipients can be present in an amount ranging from 0 to 99.9 wt-% based on the weight of the enzymatic pruritic composition.

In some embodiments, the enzymatic pruritic composition can also include wetting agents, buffers, gelling agents or emulsifiers. Other excipients could include various water-based buffers ranging in pH from 5.0-7.5, surfactants, silicones, polyether copolymers, vegetable and plant fats and oils, essential oils, hydrophilic and hydrophobic alcohols, vitamins, monoglycerides, laurate esters, myristate esters, palmitate esters, and stearate esters. In some embodiments, the enzymatic pruritic composition can be in a form including, but not limited to, liquid, gel, paste, cream, emulsion, combinations thereof, and the like.

In some embodiments, the enzymatic pruritic composition is lyophilized to a dry powder. The lyophilized enzymatic pruritic composition may be used in powder form, or the powder may be further processed into solutions, creams, lotions, gels, pastes, balms, sprays, foams, aerosols, films, or other formulations.

The addition of surfactant emulsifiers to form emulsions facilitates compatibilization with organic solvents. Examples of organic solvents useful include, but are not limited to, non-stinging solvents, such as volatile silicone solvents and volatile alkanes to form water-in-oil or oil-in-water emulsions, reverse emulsions, miniemulsions (nanoemulsions), microemulsions and reverse microemulsions. Non-stinging volatile silicone solvents include, but are not limited to, low molecular weight polydimethylsiloxane, such as hexamethyldisiloxane or octamethyltrisiloxane; low molecular weight cyclic siloxanes, such as hexamethylcyclotrisiloxane or octamethylcyclotetrasiloxane; a linear, branched or cyclic alkane, such as propane, butane, and isobutane (aerosols under pressure), pentane, hexane, heptane, octane, isooctane, and isomers thereof, petroleum distillates, and cyclohexane; chlorofluorocarbons, such as, trichloromonofluoromethane, dichlorodifluoromethane, and dichlorotetrafluoroethane; fluorocarbons, such as, tetrafluoroethane, heptafluoropropane, 1,1-difluoroethane, pentafluoropropane, perfluoroheptane, perfluoromethylcyclohexane; hydrofluoroalkanes, such as aerosols of 1,1,1,2,-tetrafluoroethane and 1,1,1,2,3,3,3-heptafluoropropane, combinations thereof and the like; and volatile gases under pressure, such as liquid carbon dioxide; or a mixture thereof. As will be understood, when stored under high pressure, carbon dioxide can be present in the form of a liquid at room temperature. In some embodiments, the volatile solvent can be hexamethyldisiloxane, isooctane, and mixtures thereof. The volatile solvent can be hexamethyldisiloxane. In some embodiments, solvents can be present in an amount ranging from 0 wt % to 99.9 wt % based on the weight of the enzymatic pruritic composition.

Water-soluble viscosity builders useful herein for addition to aqueous solutions of α-amylase include, but are not limited to, methylcellulose, hydroxyethylcellulose, hydroxypropylcellulose, hydroxypropylmethylcellulose, carboxymethylcellulose, guar gum, hydroxypropylguar, hydroxypropylmethylguar, carboxymethylguar, carboxymethylchitosan, locust bean gum, carrageenan, xanthan gum, gellan gum, Aloe vera gel, scleroglucan, schizophyllan, gum arabic, tamarind gum, poly(vinyl alcohol), poly(ethylene oxide), poly(ethylene glycol), poly(methyl vinyl ether), Carbomer and its salts, poly(acrylic acid) and its salts, poly (methacrylic acid) and its salts, sodium poly(2-acrylamido-2-methylpropanesulfonate), polyacrylamide, poly(N,N-dimethylacrylamide), poly(N-vinylacetamide), poly(N-vinylformamide), poly(2-hydroxyethyl methacrylate), poly (glyceryl methacrylate), poly(N-vinylpyrrolidone), poly(N-isopropylacrylamide) and poly(N-vinylcaprolactam), the latter two hydrated below their Lower Critical Solution Temperatures, and the like, and combinations thereof.

In some embodiments, soluble polymers that are neutral in charge and are not enzymatically degradable by amylase can be used as viscosity builders. Examples of such viscosity builders include, but are not limited to, poly(ethylene oxide), poly(ethylene glycol), poly(vinyl alcohol), and poly(N-vinylpyrrolidone). Other viscosity builders useful in the enzymatic pruritic compositions described herein include, but are not limited to, neutral polysaccharides that have β-linkages between monosaccharide units such as in methylcellulose, hydroxyethylcellulose, hydroxypropylcellulose, hydroxypropylmethylcellulose, as well as, polysaccharides that include glycosidic linkages that are not α-1-4 linkages, such as in guar and gellan, and the like. Still other viscosity builders useful in the enzymatic pruritic compositions described herein include, but are not limited to, those that are anionic in charge, such as Carbomer and its salts, poly (acrylic acid) and it salts, and poly(methacrylic acid) and its salts. Such viscosity builders may be employed in amounts ranging from about 0.01 to about 50.0 weight percent for preparation of various forms, including viscous gels or pastes. Viscosity builders can be present in amounts ranging from 0.1 to 45 wt %, or from 0.5 to 25 wt %, or from 1 to 10 wt %.

Essential oils can also be added to the formulation as fragrance or aromatic agents, and/or as antimicrobial agents. Examples of essential oils useful in the enzymatic ocmpositions described herein include, but are not limited to, thymol, menthol, sandalwood, camphor, cardamom, cinnamon, jasmine, lavender, geranium, juniper, menthol, pine, lemon, rose, eucalyptus, clove, orange, oregano, mint, linalool, spearmint, peppermint, lemongrass, bergamot, citronella, cypress, nutmeg, spruce, tea tree, wintergreen (methyl salicylate), vanilla, combinations thereof, and the like. In some embodiments, the essential oils can be selected from thymol, sandalwood oil, wintergreen oil, eucalyptol, pine oil, and combinations thereof. In some embodiments, essential oils can be present in an amount ranging from 0 to 5 wt % based on the weight of the enzymatic pruritic composition.

In some embodiments, chlorophyllin can be used to control odor and to provide anti-inflammatory properties. In some embodiments, chlorophylin can be present in an amount ranging from 0 to 5 wt % based on the weight of the enzymatic pruritic composition.

In certain embodiments, the amount of non-proteolytic enzymatic component in the enzymatic pruritic composition can be 100 wt %, or at least 99.5 wt %, or at least 99 wt %, or at least 95 wt %, or at least 90 wt %, or at least 85 wt %, or at least 80 wt %. In some embodiments, the amount of non-proteolytic enzymatic component in the enzymatic pruritic composition can be up to 100 wt %, or up to 99.5 wt %, or up to 99 wt %, or up to 95 wt %, or up to 90 wt %, or up to 85 wt %, or up to 80 wt %. In some embodiments, the amount of non-proteolytic enzymatic component in the enzymatic pruritic composition can be at least 0.001 wt %, or at least 0.01 wt %, or at least 0.05 wt %, or at least 0.075 wt %, or at least 0.1 wt %, or at least 0.15 wt %.

In some embodiments, the amount of amylase in the enzymatic pruritic composition can be 100 wt %, at least 99.5 wt %, at least 99 wt %, at least 95 wt %, at least 90 wt %, at least 85 wt %, or at least 80 wt %. In some embodiments, the amount of amylase in the non-proteolytic enzymatic component can be 100 wt %, at least 99.5 wt %, at least 99 wt %, at least 95 wt %, at least 90 wt %, at least 85 wt %, or at least 80 wt %, with the remainder of the non-proteolytic enzymatic component (20 wt % or less, 15 wt % or less, 10 wt % or less, 5 wt % or less, 1 wt % or less, 0.5 wt % or less) can be other non-proteolytic enzymes. The amount of α-amylase can be at least 10 wt-%, at least 20 wt-%, at least 30 wt-%, at least 40 wt-%, at least 50 wt-%, at least 60 wt-%, at least 70 t-%, at least 80 wt-%, at least 90 wt-%, or 100 wt-% of the amylase content. Non-amylase, non-proteolytic enzymes useful in the compositions described herein include, but are not limited to, hydrolytic, lytic, and oxidative/reductive enzymes selected from the group consisting of lipases, hyaluronidases, chondroitinases, heparanases, heparinases, peroxidases, xylanases, nucleases, phospholipases, esterases, phosphatases, isoamylases, maltases, glycosylases, galactosidases, cutinases, lactases, inulases, pectinases, mannanases, glucosidases, invertases, pectate lyases, reductases, oxidases, phenoloxidases, lipoxygenases, ligninases, pullulanases, tannases, pentosanases, glucanases, arabinosidases, sulfatases, cellulases, hemicellulases, laccases, mixtures thereof, and the like.

The enzymatic pruritic composition can include an aqueous media. In some embodiments, the aqueous media can have a pH in the range 4.5-8.0, or 5.5 to 7.5. In some embodiments, the enzymatic pruritic composition can have an osmolality of 10-340 mOsm/kg. Where the pruritic composition is an aqueous-based solution or gel, a water-soluble polymer can be added to increase solution viscosity and to prolong residence time of the enzymatic pruritic composition on the on surface of pruritic skin.

In some embodiments, the enzymatic pruritic composition comprises a penetration enhancer in order to enhance transdermal delivery of the solutions, gels, creams, lotions, pastes, balms, aerosols, and sprays described herein. Penetration enhancers useful in the enzymatic pruritic compositions described herein include, but are not limited, fatty acids such as branched and linear $C_6$-$C_{18}$ saturated acids, unsaturated acids, such as $C_{14}$ to $C_{22}$, oleic acid, cis-9-octadecenoic acid, linoleic acid, linolenic acid, fatty alcohols, such as saturated $C_8$-$C_{18}$ terpenes, such as d-limonene, α-pinene, 3-carene, menthone, fenchone, pulegone, piperitone, eucalyptol, chenopodium oil, carvone, menthol, α-terpineol, terpinen-4-ol, carveol, limonene oxide, pinene oxide, cyclopentane oxide, triacetin, cyclohexane oxide, ascaridole, 7-oxabicylco[2,2,1]heptane, 1,8-cineole, glycerol monoethers, glycerol monolaurate, glycerol monooleate, isostearyl isostearate, isopropyl myristate, isopropyl palmitate, isopropyl lanolate, pyrrolidones, such as N-methyl-2-pyrrolidone, 1-ethyl-2-pyrrolidone, 5-methyl-2-pyrrolidone, 1,5-dimethyl-2-pyrrolidone, 2-pyrrolidone-5-carboxylic acid, N-hexyl-2-pyrrolidone, N-lauryl-2-pyrrolidone, 1-dodecylazacycloheptan-2-one, 4-decyloxazolidin-2-one, N-dodecylcaprolactam, and 1-methyl-3-dodecyl-2-pyrrolidone N-n-butyl-N-n-dodecylacetamide, N,N-di-n-dodecylacetamide, N-cycloheptyl-N-n-dodecylacetamide and N,N-di-n-propyldodecanamide, urea, 1-dodecylurea, 1,3-didodecylurea, 1,3-diphenyl urea, dimethyl sulfoxide, decylmethyl sulfoxide, tetradecylmethyl sulfoxide, cyclodextrins, and combinations thereof. Also effective penetration enhancers include 1-alkyl-2-piperidinones, 1-alkyl-2-azacycloheptanones, such as 1-dodecylazacycloheptan-2-one, 1,2,3-alkanetriols, such as 1,2,3-nonanetriol, 1,2-alkanediols, n-, 2-(1-alkyl)-2-methyl-1,3-dioxolanes, oxazolidinones, such as 4-decyloxazolidin-2-one, N,N-dimethylalkanamides, 1,2-dihydroxypropyl alkanoates, such as 1,2-dihydroxypropyl decanoate, 1,2-dihydroxypropyl octanoate, sodium deoxycholate, trans-3-alken-1-ols, cis-3-alken-1-ols, trans-hydroxyproline-N-alkanamide-C-ethyl-amide, and combinations thereof. In some embodiments, the penetration enhancers can include hydrophobic esters isopropyl myristate, isopropyl palmitate, or combinations thereof.

Because of the possibly of infection in damaged and irritated tissue, the enzymatic pruritic compositions can include a biological agent in an amount sufficient to hinder or eradicate microorganisms. Such biological agents include, but are not limited to, antibiotics, antiseptics, anti-infective agents, antimicrobial agents, antibacterial agents, antifungal agents, antiviral agents, antiprotozoal agents, sporicidal agents, and antiparasitic agents. In some embodiments, the biological agent is biodegradable and non-cytotoxic to human and animal cells. Useful biocidal agents include, but are not limited to, biguanides, such as poly (hexamethylene biguanide hydrochloride) (PHMB), a low molecular weight synthetic cationic biguanide polymer, chlorhexidine and its salts, such as chlorhexidine digluconate (CHG), and alexidine and its salts, where the latter two are bis(biguanides).

In some embodiments, the biguanide is PHMB because of its high biocidal activity against microorganisms, combined with its biodegradation and low cytotoxicity. PHMB is primarily active against Gram negative and Gram positive bacteria, fungi, and viruses. In contrast to antibiotics, which are considered regulated pharmaceutical drugs, to which bacterial resistance can occur, such resistance does not occur with PHMB. In general, an antimicrobial agent is defined herein as a substance that kills microorganisms or inhibits their growth or replication, while an anti-infective agent is defined as a substance that counteracts infection by killing infectious agents, such as microorganisms, or preventing them from spreading. Often, the two terms are used interchangeably. As used herein, PHMB is considered an antimicrobial agent.

In some embodiments, the enzymatic pruritic composition is an aqueous enzymatic pruritic composition. In some embodiments, aqueous enzymatic pruritic compositions described herein can include biocidal PHMB at a concentration ranging from 0.01 wt % (100 ppm) to 1 weight % (10,000 ppm), or ranging from 0.05 wt % (500 ppm) to 0.5 wt % (5,000 ppm), or ranging from 0.1 wt % (1,000 ppm) to 0.15 wt % (1,500 ppm) based on the total weight of the enzymatic pruritic composition. Chlorhexidine and its salts can be added to the antimicrobial compositions in concentrations ranging from 10 ppm (0.001 wt %) to 20,000 ppm (2.0 wt %), while alexidine and its salts can be used in concentrations ranging from 10 ppm (0.001 wt %) to 350 ppm (0.035 wt %), with both percentages being based on the total weight of the enzymatic pruritic compositions.

The dosage at which the therapeutic amylase compositions are administered to pruritic skin is dependent upon the source of the amylase, the activity (i.e., the number of units involved), the size of irritated tissue, the age of the patient, and the incidence of infection. The amount of therapeutic amylase that may be administered up to twice per day can range from application of a powder (at 100 wt %) to a dilute solution (of about 0.001 wt %). In some embodiments, the activity of the amylase can range from 250 Units to 250,000 Units per gram of enzyme in 1 gram of enzymatic pruritic composition. In clinical instances of pruritus, application can be performed by trained medical personnel. The amylase method of ameliorating pruritus can be performed in combination with other known methods of desensitizing the skin to itching or to reducing inflammation.

The enzymatic pruritic composition may be applied topically to the irritated tissue as needed to reduce pruritus and, if present, irritation and inflammation. For example, in some embodiments, the enzymatic pruritic composition may be in contact with the irritated or inflamed tissue for about 1 to 48 hours, 1 to 24 hours, 1 to 12 hours, 1 to 8 hours, 1 to 4 hours, or 1 to 2 hours, or from 1 to 60 minutes to 1 to 5 minutes before removal. In some embodiments, the method of relieving pruritus can include applying the enzymatic pruritic composition periodically (e.g., every hour, every 2 hours, every 3 hours, every 4 hours, every 6 hours, every 8 hours, etc.) while the pruritus persists. Removal of the enzymatic pruritic composition is preferably by wiping or by rinsing with saline or water. These steps may be repeated as needed. A wide variety of pruritic skin areas can be treated with the enzymatic pruritic composition described herein, including surrounding areas of full and partial thickness burn wounds, diabetic ulcers, ulcerative lesions, principally pressure (decubitus) ulcers, venous ulcers, trophic ulcers, surgical wounds such as amputation, incisions, traumatic and pyogenic wounds, donor and receptor skin graft wounds, dermatological abrasions, eczema, rashes, dry skin, pimples, contact dermatitis, psoriasis, rosacea, seborrheic dermatitis, insect bites, acne, cysts, blisters, radiation wounds, chemical and biological irritants, sunburn, and frostbite.

Similarly, a kit described herein can include instructions to apply the enzymatic pruritic composition periodically (e.g., every hour, every 2 hours, every 3 hours, every 4 hours, every 6 hours, every 8 hours, etc.) while the pruritus persists. In some embodiments, the instructions can include removing or rinsing the enzymatic pruritic composition (e.g., by wiping or rinsing) a set time period following application of the enzymatic pruritic composition.

As used herein, proteolytic enzymes break (cleave, digest) the long chainlike polymer molecules of proteins into shorter fragments of peptides and, eventually, into their basic components of amino acids.

As used herein, a covalent bond that is formed between a carbohydrate molecule and another molecule, particularly between two monosaccharides moieties, is a glycosidic bond or glycodisic linkage.

As used herein, α-1,4-glycosidic linkages are bonds that are normally formed between the carbon-1 on one sugar and the carbon-4 on another sugar moiety in a polysaccharide. A α-glycosidic bond is formed when the —OH group on carbon-1 is below the plane of the glucose ring. On the other hand, a β-glycosidic bond is formed when it is above the plane. For example, cellulose is formed of glucose molecules linked by 1-4 β-glycosidic bonds, whereas starch is composed of 1-4 α-glycosidic bonds.

As used herein, α-amylase includes naturally occurring α-amylases as well as recombinant α-amylases, wherein recombinant α-amylase means an α-amylase in which the DNA sequence encoding the naturally occurring α-amylase is modified to produce a mutant DNA sequence that encodes the substitution, insertion or deletion of one or more amino acids in the α-amylase sequence compared to the naturally occurring α-amylase.

As used herein, an "isoenzyme" is a chemically distinct form of an enzyme that performs the same biochemical function.

As used herein, the amount of enzyme utilized is expressed in weight percent and its activity is given in Units of activity per gram, where a "Unit" is defined as the amount of enzyme that catalyzes the conversion of 1 micromole of substrate per minute.

As used herein, the term "amylolytic" is characterized by or capable of the enzymatic digestion of starch into dextrins and sugars.

As used herein, the term "lipolytic" pertains to the hydrolysis of lipids, particularly the hydrolysis of triglycerides into glycerol and three fatty acids.

As used herein, the term "keratolytic agent" pertains to a material causing the softening and shedding of the outer layer of the skin.

As used herein, "surfactant" has its standard meaning and includes emulsifying agents, emulsifiers, detergents, and surface-active agents.

As used herein, "microemulsion" is has its standard meaning and includes thermodynamically stable mixtures of oil, water (and/or hydrophilic compound) and surfactant. Microemulsions include three basic types: direct (oil dispersed in water, o/w), reverse (water dispersed in oil, w/o) and bicontinuous. Microemulsions are optically clear because the dispersed micelles have a diameter that is less than the wavelength of visible light (e.g., less than 380 nanometers, less than 200 nanometers, or less than 100 nanometers) in diameter. In the absence of opacifiers, microemulsions are optically clear, isotropic liquids.

As used herein, "reverse microemulsion" has its standard meaning and includes a microemulsion comprising a hydrophilic phase suspended in a continuous oil phase. A reverse microemulsion can include droplets of a hydrophilic phase (e.g., water, alcohol, or a mixture of both) stabilized in an oil phase by a reverse emulsion surfactant. In such instances, a hydrophilic active agent can be solubilized in the droplets. However, in other instances, the reverse microemulsion can be free of water and/or alcohol, and the hydrophilic active agent can be directly solubilized in the oil phase by the reverse emulsion surfactant.

As used herein, "hydrophilic" has its standard meaning and includes compounds that have an affinity to water and can be ionic or neutral or have polar groups in their structure that attract water. For example, hydrophilic compounds can be miscible, swellable or soluble in water.

As used herein, "aqueous" compositions refer to a spectrum of water-based solutions including, but not limited to, homogeneous solutions in water with solubilized components, emulsified solutions in water stabilized by surfactants or hydrophilic polymers, and viscous or gelled homogeneous or emulsified solutions in water.

As used herein, an enzyme is "soluble" or "solubilized" if the amount of enzyme present in the solvent system is dissolved in the solvent system without the enzyme forming a precipitate or visible, swollen gel particles in solution.

As used herein, "non-stinging" means that the formulation does not cause a sharp, irritatingly, burning or smarting pain as a result of contact with a biological surface.

As used herein, "volatile" has its standard meaning, that is, it can evaporate rapidly at normal temperatures and pressures. For example, a solvent is volatile if one drop (0.05 mL) of the solvent will evaporate completely between 20-25° C. within 5 minutes, or within 4 minutes, or within 3 minutes, or within 2 minutes, or within 1 minute, or within 30 seconds, or within 15 seconds.

As used herein, an "antimicrobial agent" is defined as a substance that kills microorganisms or inhibits their growth or replication, while an "anti-infective agent" is defined as a substance that counteracts infection by killing infectious agents, such as microorganisms, or preventing them from spreading. Often, the two terms are used interchangeably. Antibiotics are considered those substances that were originally produced by a microorganism or synthesized with active properties that can kill or prevent the growth of another microorganism. The term "antibiotic" is commonly used to refer to almost any prescribed drug that attempts to eliminate infection. Antimicrobial agents do not cause biocidal resistance such as can occur with antibiotics, wherein antibiotic resistance to a drug can occur. Antimicrobial agents have a broad spectrum of activity against bacteria, fungi, viruses, protozoa and prions. Examples of antimicrobial agents include biguanides, such as poly(hexamethylene biguanide hydrochloride) (PHMB), chlorhexidine and its salts, alexidine and its salts, povidone/iodine, cadexomer iodine, silver sulfadiazine, nanocrystalline silver, ionic silver, honey, dilute bleaching agents such as sodium hypochlorite and hypochlorous acid, hydrogen peroxide, organic peroxides such as benzoyl peroxide, alcohols such as ethanol and isopropanol, anilides such as triclocarban, bisphenols such as triclosan, chlorine compounds, and quaternary ammonium compounds such as benzalkonium chloride, benzethonium chloride, cetyltrimethylammonium chloride, cetylpyridinium chloride, and alkyltrimethylammonium bromides, as well as miconazole, clotrimazole, ketoconazole, fluconazole, crystal violet, amphotericin B, tee tree oil, combinations thereof, and the like. Biguanides, such as PHMB, are useful in the enzymatic pruritic compositions described herein.

A polymeric biguanide useful in the enzymatic pruritic compositions described herein is poly(hexamethylene biguanide), commercially available from Arch Chemicals, Inc., Smyrna, Ga. under the trademark Cosmocil™ CQ. Poly (hexamethylene biguanide) polymers are also referred to as poly(hexamethylene biguanide) (PHMB), poly(hexamethylene bisbiguanide) (PHMB), poly(hexamethylene guanide) (PHMB), poly(aminopropyl biguanide) (PAPB), poly [aminopropyl bis(biguanide)] (PAPB), polyhexanide and poly(iminoimidocarbonyl)iminohexamethylene hydrochloride; however, PHMB is the preferred abbreviation. PHMB is a broad spectrum antimicrobial and has been used in contact lens multipurpose solutions, wound rinsing solutions, wound dressings, perioperative cleansing products, mouthwashes, surface disinfectants, food disinfectants, veterinary applications, cosmetic preservatives, paper preservatives, secondary oil recovery disinfectants, industrial water treatments, and in swimming pool cleaners. It is normally obtained commercially in the hydrochloride form in water. Other antimicrobial polymers can also be added, such as polyquaternium 1, polyquaternium 6, polyquaternium 10, cationic guar, and water-soluble derivatives of chitosan.

As used herein, "antibiotic resistance" is the ability of bacteria and other microorganisms to resist the effects of an antibiotic to which they were once susceptible.

The enzymatic pruritic composition described herein can include a biocidal monoalkyl glycol, glycerol alkyl ether, and monoacyl glycerol at a combined concentration of from 0.05 wt % (500 ppm) to 4 wt % (4,000 ppm), or from 0.1 wt % (1,000 ppm) to 1 wt % (10,000 ppm), or from 0.4 wt % (4,000 ppm) to 0.6 wt % (6,000 ppm) based on the weight of the enzymatic pruritic composition. The monoalkyl glycol, glycerol alkyl ether, and monoacyl glycerol can be hydrophobic.

As used herein, "hydrophobic" refers to repelling water, being insoluble or relatively insoluble in water, and lacking an affinity for water. Hydrophobic compounds with hydrophilic substituents, such as vicinal diols, may form emulsions in water, with or without added surfactant.

As used herein, "amphoteric" refers to a mixture of cationic and anionic charges on a molecule or polymer in which overall charge is locally pH dependent, whereas "ampholytic" has an equal number of cationic and anionic charges over a broad pH range.

As used herein, "pruritus" refers to an intense sensation of itching.

As used herein, "inflammation" refers to a localized reaction that produces redness, warmth, swelling, and pain as a result of infection, irritation, or injury. Inflammation can be external or internal.

As used herein, "irritation" of the skin refers to a reaction to an irritant or an inducement of discomfort resulting in itchiness and inflammation.

As used herein, an "enzyme unit" (U) is generally defined as the amount of the enzyme that produces a certain amount of enzymatic activity, that is, the amount that catalyzes the conversion of 1 micromole of substrate per minute.

As used herein, an "excipient" is a usually inert substance that forms a vehicle, such as a liquid, fluid, or gel, that solubilizes or disperses a biological formulation, such as an enzyme.

Examples of monoalkyl glycols useful in the enzymatic pruritic compositions described herein include, but are not limited to, 1,2-propanediol (propylene glycol), 1,2-butanediol, 1,2-pentanediol, 1,2-hexanediol, 1,2-heptanediol, 1,2-octanediol (caprylyl glycol), 1,2-nonanediol, 1,2-decanediol, 1,2-undecanediol, 1,2-dodecanediol, 1,2-tridecanediol, 1,2-tetradecanediol, 1,2-pentadecanediol, 1,2-hexadecanediol, 1,2-heptadecanediol and 1,2-octadecanediol. Non-vicinal glycols can also be added to enhance biocidal activity. Exemplary, non-vicinal glycols include, but are not limited to, 2-methyl-2,4-pentanediol, 1,3-butanediol, diethylene glycol, triethylene glycol, and glycol bis(hydroxyethyl) ether.

Examples of glycerol alkyl ethers useful in the enzymatic pruritic compositions described herein include, but are not limited to, 1-O-heptylglycerol, 1-O-octylglycerol, 1-O-nonylglycerol, 1-O-decylglycerol, 1-O-undecylglycerol, 1-O-dodecylglycerol, 1-O-tridecylglycerol, 1-O-tetradecylglycerol, 1-O-pentadecylglycerol, 1-O-hexadecylglycerol (chimyl alcohol), 1-O-heptadecylglycerol, 1-O-octadecylglycerol (batyl alcohol), 1-O-octadec-9-enyl glycerol (selachyl alcohol), glycerol 1-(2-ethylhexyl) ether (also known as octoxyglycerin, 2-ethylhexyl glycerin, 3-(2-ethylhexyloxy)propane-1,2-diol, and Sensiva® SC 50), glycerol 1-heptyl ether, glycerol 1-octyl ether, glycerol 1-decyl ether, and glycerol 1-dodecyl ether, glycerol 1-tridecyl ether, glycerol 1-tetradecyl ether, glycerol 1-pentadecyl ether, glycerol 1-hexadecyl ether and glycerol 1-octadecyl ether.

Examples of monoacyl glycerols useful in the enzymatic pruritic compositions described herein include, but are not limited to, 1-O-decanoylglycerol (monocaprin), 1-O-undecanoylglycerol, 1-O-undecenoylglycerol, 1-O-dodecanoylglycerol (monolaurin, also called glycerol monolaurate and Lauricidin®), 1-O-tridecanoylglycerol, 1-O-tetradecanoylglycerol (monomyristin), 1-O-pentadecanoylglycerol, 1-O-hexadecanoylglycerol, 1-O-heptadecanoylglycerol, and 1-O-octanoylglycerol (monocaprylin). In general, glycerols substituted in the 1-O-position are more preferred than those substituted in the 2-O-position, or disubstituted in the 1-0 and 2-0 positions.

The enzymatic pruritic compositions can include one or more additional surfactants for cleansing of the skin surface. Suitable surfactants include, but are not limited to cationic, anionic, nonionic, amphoteric and ampholytic surfactants. In some embodiments, the surfactants are non-stinging or low irritant nonionic and amphoteric surfactants. In some embodiments, the surfactant can be present in an amount ranging from 0 to 10 wt % based on the weight of the enzymatic pruritic composition. The surfactants can have an HLB (hydrophilic-lipophilic balance) value of 18-30 in order to not distort the catalytic structure of amylase in solution as well as not hindering the biocidal activity of any added antimicrobial agents, while facilitating a non-cytotoxic solution. The high values of the HLB represent surfactants that are more hydrophilic than those with lower HLB values.

Suitable nonionic surfactants include, but are not limited to, the ethylene oxide/propylene oxide block copolymers of poloxamers, reverse poloxamers, poloxamines, and reverse poloxamines. Poloxamers and poloxamines are preferred, and poloxamers are most preferred. Poloxamers and poloxamines are available from BASF Corp. under the respective trade names of Pluronic® and Tetronic®. Suitable Pluronic surfactants comprise but are not limited to Pluronic F38 having a HLB of 31, Pluronic F68 having a HLB of 29, Pluronic 68LF having a HLB of 26, Pluronic F77 having a HLB of 25, Pluronic F87 having a HLB of 24, Pluronic F88 having a HLB of 28, Pluronic F98 having a HLB of 28, Pluronic F108 having a HLB of 27, Pluronic F127 (also known as Poloxamer 407) having a HLB of 18-23, and Pluronic L35 having a HLB of 19. An exemplary poloxamine surfactant of this type is Tetronic 1107 (also known as Poloxamine 1107) having an HLB of 24.

In addition to the above, other neutral surfactants may be added, such as for example polyethylene glycol esters of fatty acids, e.g., coconut, polysorbate, polyoxyethylene or polyoxypropylene ethers of higher alkanes ($C_{12}$-$C_{18}$), polysorbate 20 available under the trademark Tween 20, polyoxyethylene (23) lauryl ether available under the trademark Brij 35, polyoxyethylene (40) stearate available under the trademark Myrj 52, and polyoxyethylene (25) propylene glycol stearate available under the trademark Atlas G 2612, all available by Akzo Nobel, Chicago, Ill. Other neutral surfactants include nonylphenol ethoxylates such as nonylphenol ethoxylates, Triton X-100, Brij surfactants of polyoxyethylene vegetable-based fatty ethers, polyoxyethylene ethers, Tween 80, decyl glucoside, and lauryl glucoside.

Amphoteric surfactants suitable for use in antimicrobial compositions according to the present invention include materials of the type offered commercially under the trademark Miranol (Rhodia). Another useful class of amphoteric surfactants is exemplified by betaines, including cocoamidopropyl betaine, undecylenamidoalkylbetaine, and lauramidoalkylbetaine and sodium cocoamphoacetate. Amphoteric surfactants are very mild and have excellent dermatological properties, making them particularly suited for use in personal care applications, particularly regarding treatment for pruritus and irritation.

Suitable reverse emulsion surfactants include sodium bis(2-ethylhexyl)sulfosuccinate (Aerosol AOT, also called AOT, docusate sodium, DSS, Aerosol OT, and sodium 1,4-bis(2-ethylhexoxy)-1,4-dioxobutane-2-sulfonate), sodium bis(tridecyl)sulfosuccinate, bis(dialkyl)sulfosuccinate salts, copolymers of polydimethylsiloxane and polyethylene/polypropylene-oxide, polyoxypropylene (12) dimethicone, cetyl PEG/PPG-10/1 dimethicone, hexyl laurate and polyglyceryl-4-isostearate, PEG-10 dimethicone, sorbitan monolaurate, sorbitan monooleate, polyoxyethylenesorbitan trioleate, polyoxyethylene octyl phenyl ether, polyoxyethylene 10 cetyl ether, polyoxyethylene 20 cetyl ether, polyethylene glycol tert-octylphenyl ether, sodium di(2-ethylhexyl)phosphate, sodium di(oleyl)phosphate, sodium di(tridecyl)phosphate, sodium dodecylbenzenesulfonate, sodium 3-dodecylaminopropanesulfonate, sodium 3-dodecylaminopropionate, sodium N-2-hydroxydodecyl-N-methyltaurate, lecithin, sucrose fatty acid esters, 2-ethylhexylglycerin, caprylyl glycol, long chain hydrophobic vicinal diols of monoalkyl glycols, monoalkyl glycerols, or monoacyl glycerols, polyoxyl castor oil derivatives, polyethylene glycol hydrogenated castor oil, tetraethylene glycol dodecyl ether, potassium oleate, sodium oleate, cetylpyridynium chloride, alkyltrimethylammonium bromides, benzalkonium chloride, didodecyldimethylammonium bromide, trioctylmethylammonium bromide, cetyltrimethylammonium bromide, cetyldimethylethylammonium bromide, and the like, with or without added alkanols such as isopropanol, 1-butanol, and 1-hexanol, and combinations thereof. The reverse emulsion surfactants can be dialkylsulfosuccinate salts, such as sodium bis(2-ethylhexyl)sulfosuccinate.

In some embodiments, the enzymatic pruritic composition can include dialkylsulfosuccinates, such as sodium bis(2-ethylhexy)sulfosuccinate (AOT). Dialkylsulfosuccinates have been demonstrated to have antibacterial, anti-fungal and anti-viral properties (U.S. Pat. Nos. 4,717,737, 4,719, 235 and 4,885,310). This effect would be expected to enhance the antimicrobial and anti-infective properties of the reverse microemulsion compositions described herein.

The enzymatic pruritis compositions may also contain chlorophyllin and its water-soluble derivatives in order to reduce local inflammation, promote healing, and controlling odor, if present (U.S. Pat. No. 2,917,433).

If pain reduction is required during treatment of pruritic tissue, which may involve irritation and inflammation, the enzymatic pruritic composition can further comprise analgesic agents, anesthetic agents, and neuropathic pain agents, such as lidocaine, capsaicin, calamine lotion, benzocaine, tetracaine, prilocaine, bupivacaine, levobupivacaine, procaine, carbocaine, etidocaine, mepivacaine, nortripylene, amitriptyline, pregabalin, diclofenac, fentanyl, gabapentin, opiods, ketoconazole, non-steroidal anti-inflammatory agents, salicylates, leukotriene antagonists, combinations thereof, and the like.

The enzymatic pruritic composition may further comprise a chelating agent at a concentration of from 0 weight % to 1 weight %. For example, the chelating agent can be present in an amount of at least 0.01 wt %, or at least 0.03 wt %, or at least 0.05 wt %, or at least 0.1 wt %, or at least 0.50 wt %, or at least 0.75 wt %, or at least 1.0 wt %. The chelating agent can be selected from the group that includes, but is not limited to, ethylenediaminetetraacetic acid (EDTA), nitrilotriacetic acid, nitrilotripropionic acid, diethylenetriaminepentaacetic acid, 2-hydroxyethylethylenediaminetriacetic acid, 1,6-diaminohexamethylenetetraacetic acid, 1,2-diaminocyclohexanetetraacetic acid, O,O'-bis(2-aminoethyl)ethyleneglycoltetraacetic acid, 1,3-diaminopropanetetraacetic acid, N,N'-bis(2-hydroxybenzyl)ethylenediamine-N,N'-diacetic acid, ethylenediamine-N,N'-diacetic acid, ethylenediamine-N,N'-dipropionic acid, triethylenetetraaminehexaacetic acid, ethylenediamine-N,N'-bis(methylenephosphonic acid), iminodiacetic acid, monosodium-N-lauryl-R-iminodipropionic acid (sodium lauriminodipropionate, Deriphat® 160C), N,N-bis(2-hydroxyethyl)glycine, 1,3-diamino-2-hydroxypropanetetraacetic acid, 1,2-diaminopropanetetraacetic acid, ethylenediaminetetrakis(methylenephosphonic acid), N-(2-hydroxyethyl)iminodiacetic acid, biphosphonates, editronate, and salts thereof.

In some embodiments, a kit that includes a container containing an enzymatic pruritic composition according to any of the variations described herein, and instructions for using the enzymatic pruritic composition for treatment or pruritus is described. The instructions can include contacting the enzymatic pruritic composition with an area of skin in need of treatment for pruritus. The instructions can include repeating the contacting step at regular intervals. The regular intervals can be at least once a day, or at least twice a day (every 12 hours), or at least three times a day (every 8 hours), or as needed. The instructions can include mixing and or diluting the enzymatic pruritic composition in a solvent or other carrier liquid. The instructions can include removal of the enzymatic pruritic composition by wiping and by solvent rinsing (e.g., using soapy water).

A method of treatment of pruritus is also described. The method can include contacting an enzymatic pruritic composition according to any of the variations described herein with an area of skin experiencing pruritus, such as by a powder, liquid, gel, hydrogel, foam, paste, cream, spray, or film. In some embodiments, the enzymatic pruritic composition is applied to a sterile dressing, such as gauze, cloth, fiber, alginate, hydrocolloid, composite, or film. In some embodiments, the wound dressing is composed of natural or synthetic components, or combinations thereof. The method can also include allowing the enzymatic pruritic composition to remain on the skin for a given period of time (e.g., 1 minute, or 5 minutes, or 15 minutes, or 1 hour), The method can include repeating the contacting step at regular intervals. In some embodiments, the regular intervals can be at least once a day, or at least twice a day (every 12 hours), or at least three times a day (every 8 hours). In some embodiments, the method also includes removing the enzymatic pruritic composition from the area of skin.

It is an object of the compositions, kits, and methods described herein to provide amylase for treatment of pruritic tissue in humans and animals.

It is a further object of the compositions, kits, and methods described herein to provide amylase for treatment of irritated or inflamed tissue resulting from scratching or rubbing of pruritic tissue.

It is a further object of the compositions, kits, and methods described herein to treat pruritus and concomitant skin irritation and inflammation comprising the step of administering an effective amount of $\alpha$-amylase enzyme.

It is a further object of the compositions, kits, and methods described herein to provide carbohydrate hydrolytic enzymes for enzymatic pruritus treatment based upon the amylase family, selected from combinations of $\alpha$-amylase, with 1-amylase, and $\gamma$-amylase.

It is a further object of the compositions, kits, and methods described herein to provide for enzymatic pruritus treatment based on amylase, wherein the amount of amylase in a enzymatic pruritic composition capable of reducing or eliminating itch may be 100 wt %, at least 99.5 wt %, at least 99 wt %, at least 95 wt %, at least 90 wt %, at least 85 wt %, or at least 80 wt % of an amylase, preferably containing at least 10 wt % $\alpha$-amylase, with other non-amylase enzymes of 20 wt % or less.

It is a further object of the compositions, kits, and methods described herein to provide for enzymatic pruritus treatment wherein families of hydrolytic cleavage enzymes other than amylases include 20 wt % or less of proteases, chondroitinases, hyaluronidases, lipases, glycosidases, heparanases, dermatanases, pullulanases, N-acetylglucosaminidase, lactases, phospholipases, transglycosylases, esterases, thioester hydrolyases, sulfatases, escharases, nucleases, phosphatases, phosphodiesterases, mannanases, mannosidases, isoamylases, lyases, inulinases, keratinases, tannases, pentosanases, glucanases, arabinosidases, pectinases, cellulases, chitinases, xylanases, cutinases, pectate lyases, hemicellulases, combinations thereof, and the like.

It is a further object of the compositions, kits, and methods described herein to provide for enzymatic pruritus treatment wherein families of enzymes other than amylases include 20 wt % or less of oxidases, peroxidases, glucose oxidases, catalases, oxidoreductases, phenoloxidases, laccases, lipoxygenases, isomerases, and ligninases.

It is a further object of the compositions, kits, and methods described herein to provide for enzymatic pruritus treatment based upon $\alpha$-amylase, wherein the $\alpha$-amylase is administered in the form of a powder, gel, paste, liquid, ointment, balm, cream, foam or spray.

It is a further object of the compositions, kits, and methods described herein to provide for enzymatic pruritus treatment based upon $\alpha$-amylase, wherein the $\alpha$-amylase is administered on or in a bandage, mesh, film, foam, coating or dressing of natural or synthetic origin.

It is a further object of the compositions, kits, and methods described herein to provide for enzymatic pruritus treatment based upon $\alpha$-amylase that is administered topically.

It is a further object of the compositions, kits, and methods described herein to provide for enzymatic pruritus treatment based upon α-amylase, wherein the α-amylase is applied in a hydrophilic or aqueous medium.

It is a further object of the compositions, kits, and methods described herein to reduce irritation and inflammation resulting from pruritus by treatment with α-amylase.

It is a further object of the compositions, kits, and methods described herein to ameliorate pruritus by treatment with α-amylase.

It is a further object of the compositions, kits, and methods described herein to provide a pleasing fragrance to the enzymatic pruritic compositions.

It is a further object of the compositions, kits, and methods described herein to add chlorophyllin to an enzymatic pruritus treatment based upon α-amylase to reduce local inflammation, promote healing, and control odor.

It is a further object of the compositions, kits, and methods described herein to provide a dressing for amylase pruritus treatment comprised of gauze, cloth, mesh, fiber, foam, natural or synthetic fiber, mesh, hydrocolloid, alginate, hydrogel, semipermeable film, permeable film, or a natural or synthetic polymer.

It is a further object of the compositions, kits, and methods described herein to provide for preserved formulations of α-amylase.

It is a further object of the compositions, kits, and methods described herein to provide for enzymatic pruritic compositions of α-amylase.

It is a further object of the compositions, kits, and methods described herein to provide for enzymatic pruritic compositions of α-amylase that reduce or eliminate Gram positive and Gram negative bacteria.

It is a further object of the compositions, kits, and methods described herein to provide for enzymatic pruritic compositions of α-amylase that reduce or eliminate yeast.

It is a further object of the compositions, kits, and methods described herein to provide for enzymatic pruritic compositions of α-amylase based upon polymeric biguanide-containing compositions.

It is a further object of the compositions, kits, and methods described herein to provide for enzymatic pruritic compositions that incorporate antimicrobial essential oils to the α-amylase compositions.

It is a further object of the compositions, kits, and methods described herein to provide a surfactant capable of cleansing a tissue surface for α-amylase pruritus treatment.

It is a further object of the compositions, kits, and methods described herein to provide for α-amylase-based pruritus treatment a hydrophilic polymer capable of increasing viscosity or causing gelation of the formulation to increase residence time on the affected tissue.

It is a further object of the compositions, kits, and methods described herein to provide delivery of α-amylase from a hydrophobic, volatile solvent to pruritic tissue.

It is a further object of the compositions, kits, and methods described herein to provide a surfactant capable of solubilizing α-amylase into a hydrophobic, volatile solvent.

It is a further object of the compositions, kits, and methods described herein to provide a hydrophobic, volatile solvent that is non-stinging to pruritic tissue.

It is a further object to form a reverse microemulsion through the combination of a surfactant with water and a nonpolar solvent to solubilize α-amylase.

It is a further object of the compositions, kits, and methods described herein to provide an amylase formulation for treatment of pruritus and its concomitant irritated and inflamed tissue that also has antimicrobial properties.

EXAMPLES

The following ingredients and their abbreviations are used in this invention:

Enzymes

α-Amylase #1, porcine pancreas, 30 U/mg, Sigma Aldrich, A3176-500KU, lot SLBF3831V.

α-Amylase #2, porcine pancreas, (contains 0.2% protease), 230 U/mg, Lee BioSolutions, lot M60404.

α-Amylase #3, porcine pancreas, (contains 0.05% protease), 210 U/mg, Lee BioSolutions, lot P70442.

α-Amylase #4, human saliva, 117.5 U/mg, Sigma Aldrich, lot SLBB8953V.

α-Amylase #5, *Bacillus licheniformis*, 500-1500 U/mg, Sigma Aldrich, lot SLBG8595V.

α-Amylase #6, *Bacillus subtilis* spp., powder, 7278 U/mg, Dyadic International, lot ADY4001.

α-Amylase #7, *Bacillus subtilis* spp., solution, 1269 U/mg, Dyadic International, lot ASP3001.

β-Amylase, barley, 41.6 U/mg, Sigma Aldrich, lot SLBC2932V.

γ-Amylase #1, *Aspergillus niger*, 129.2 U/mg, Sigma Aldrich, lot BCBD1453V.

γ-Amylase #2, *Rhizopus* spp., MyBiosource Inc., lot 22200303.

Collagenase, Type I, *Clostridium histolyticum*, 125 U/mg, Sigma Aldrich, C0130-100UG, lot SLBH5757V.

Lipase, porcine pancreas, (contains <0.05% protease), 360 U/mg, Lee BioSolutions, 400-10, lot R24160.

Other Ingredients

AC, Antimicrobial Composition, Water, 95.5 wt %, PHMB 0.1 wt %, EDTA 0.065 wt %, P407 2 wt %, HPMC, 2 wt %, SC50, 0.3 wt %, SC10, 0.1 wt %, pH 5.5.

AOT: Aerosol AOT, sodium bis(2-ethylhexyl)sulfosuccinate, Fisher Scientific, lot 112760.

CHG, Chlorhexidine gluconate, Spectrum Chemicals, lot ZQ1023.

Chlorophylin, Sigma, MKBQ6480V.

Collagen, type I, rat tail, Corning Inc., 354236, lot 3298599.

DC 193, PEG-12 Dimethicone, Dow Corning, lot 0002250697.

Dulbecco's Phosphate Buffered Saline, DPBS, Sigma Aldrich, D8537, lot RNBC1143.

EDTA, Ethylenediaminetetraacetic acid di-, tri-sodium salts, Spectrum Chemicals, lots 1AE0430, YL0044.

Glycerin: Quality Choice, lot 519675.

HMDS: Hexamethyldisiloxane, Gelest Lot 2A-17635.

Hydroxypropylmethylcellulose (HPMC), Amerchol Corp., lot WF15012N01.

Mineral Oil, CVS, lot 5BF0201.

PHMB, Poly(hexamethylene biguanide hydrochloride), Cosmocil™ CQ, Arch Chemical, lot 11RC116995.

P407, Poloxamer 407, Pluronic F127, Spectrum Chemicals, lot 1AD0265.

PEG 400, Poly(ethylene glycol), 400 $M_n$, Sigma Aldrich, lot MKBD2642V.

Petrolatum: Vaseline, lot 02011 HU00.

Polymer JR-30M, Amerchol, lot XL2850GRXA.

SC10, Sensiva® SC 10, 1,2-Dihydroxyoctane), Schülke & Mayr, lot 1178933.

SC50, Sensiva® SC 50, Glycerol 1-(2-ethylhexyl)ether), Schülke & Mayr, lot 1179743.

Sodium Hydroxide, Puritan 50% NaOH, UN1824, lot 011043.

Urea, Sigma Aldrich, lot SLBF4607V.
Water, Deionized, adjusted to pH 7.

Collagen Gel Digestion

Proteases have been implicated in the treatment of skin disorders. In order to determine if α-amylase contained a protease, which is able to cleave a collagen gel (i.e., a protein-based gel), collagen gel digestion was studied by rheology under varied frequency conditions using α-amylase and collagenase as potential digesting enzymes. If α-amylase had no digestion of the collagen gel, its anti-pruritic activity would not be based upon any contamination by a protease, and not by hydrolysis of peptide bonds of collagen polymer chains as by collagenase.

Collagen gels were prepared at 2.0 mg/mL using collagen type I. Gels were prepared by mixing 500 µL collagen (~4.1 mg/mL), 500 µL Dulbecco's phosphate buffered saline (DPBS without calcium and magnesium), and 10 µL 1 N NaOH (diluted from Puritan 50% NaOH). Solid collagen hydrogels formed after 30 min in a 37° C. incubator. Gels were incubated at 37° C. for 24 hours with the following enzymes:

2 mg (250 U) collagenase
8 mg (250 U) α-amylase #1

Rheological testing was conducted on an Anton Paar MCR 302 rheometer using a 25 mm parallel plate (for solid gels) and 25 mm cone and plate (for completely liquefied gels, i.e., collagen gel treated with collagenase). All frequency sweeps were conducted at 37° C. and 1% strain (linear viscoelastic region as determined by a strain amplitude sweep). The data are shown in FIG. 1, for the storage and loss moduli vs. frequency, and in FIG. 2, for the complex moduli for untreated collagen gel, for amylase treated collagen gel and collagenase treated collagen gel.

Figure 1:
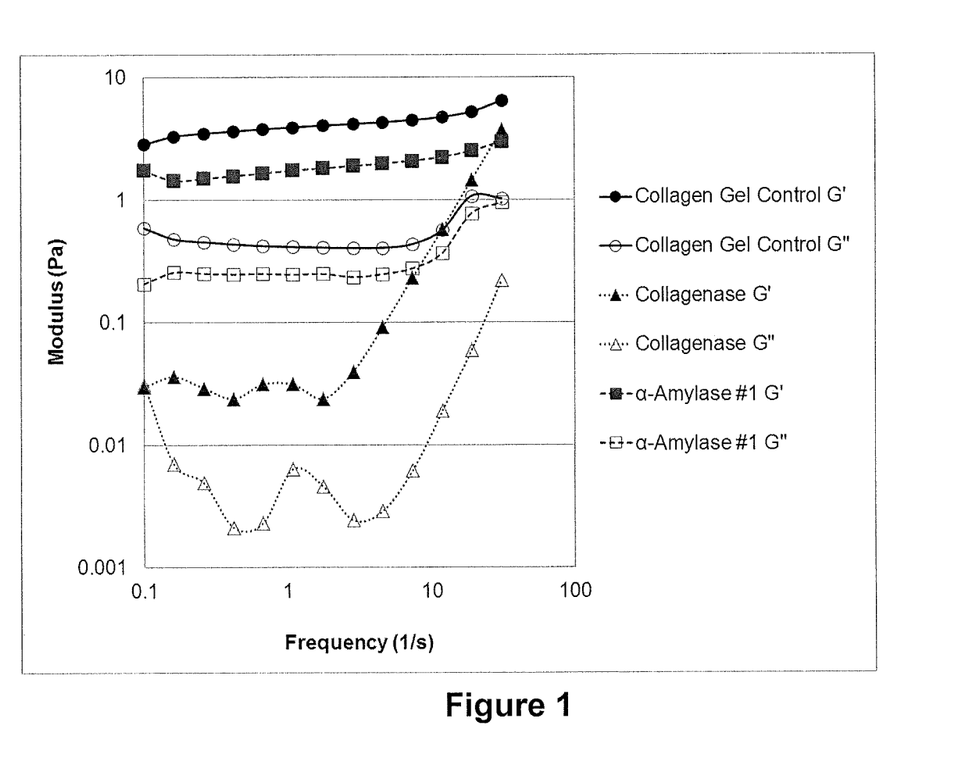
FIG. 1 is a graph of frequency versus modulus for collagen gels before and after treatment with different enzymes.

In FIG. 1, storage (G') and loss (G") moduli versus frequency are presented for untreated collagen gel controls, collagen gels treated with 250 U collagenase, and collagen gels treated with 250 U α-amylase #1. The storage modulus represents the solid-like nature and the loss modulus represents the liquid-like nature of the viscoelastic collagen gel. There is no significant difference between storage and loss moduli between the untreated collagen gel and the gel treated with α-amylase, which demonstrates no collagen (protein) gel digestion by α-amylase. The protease collagenase completely liquefied the collagen gel, which is demonstrated by the significantly lower storage and loss moduli.

Figure 2:
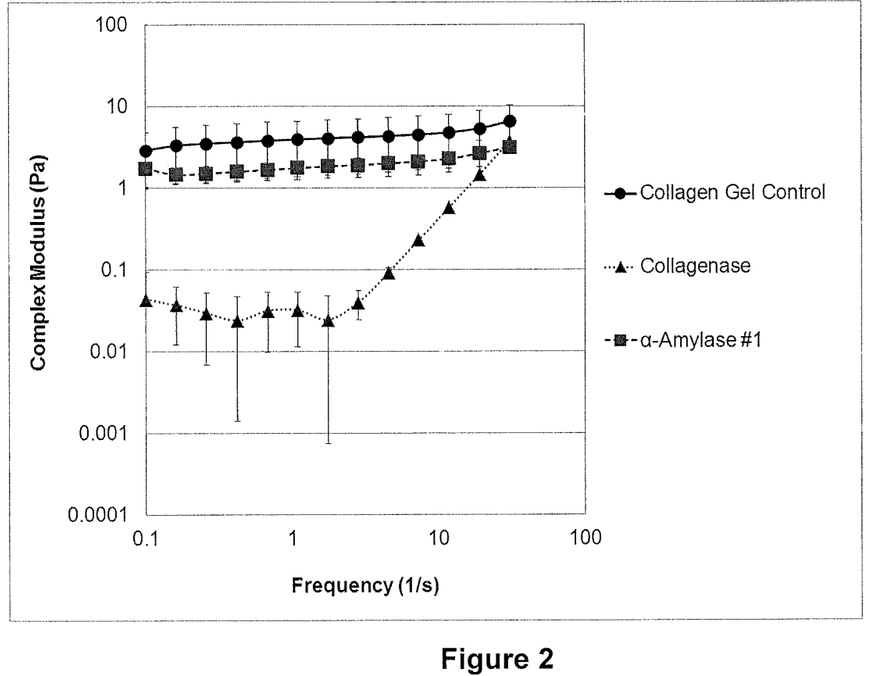
FIG. 2 is a graph of frequency versus complex modulus for collagen gels before and after treatment with different enzymes.

In FIG. 2, complex modulus (G*) is plotted versus frequency for untreated collagen gel controls, collagen gels treated with 250 U collagenase, and collagen gels treated with 250 U amylase #1. Complex modulus accounts for the storage modulus (solid-like behavior) and loss modulus (liquid-like behavior), which correlates with the gel's stiffness. α-Amylase #1 does not digest the collagen gels compared to the untreated collagen gel control (no statistically significant difference in complex moduli).

These figures demonstrate that collagenase, a protease, completely liquefied the collagen gels within 24 hours, whereas α-amylase, a protein enzyme noted for cleavage of α-linked polysaccharides such as starch and glycogen, did not digest the collagen gel compared to the untreated collagen gel control (no statistically significant difference in storage moduli, loss moduli, or complex moduli). Moduli are observed to increase with frequency due to the viscoelastic nature of the polymer (collagen) tested. At high frequencies, the collagen polymer chains do not have time to relax, resulting in an observed stiffer viscoelastic behavior. The data for collagen gel treated with collagenase appears noisy due to the liquid-like nature resulting from the digestion of the collagen gel. Collagenase completely degraded and liquefied the collagen gel, and the resulting enzymatically degraded solution had to be evaluated using cone and plate geometry. While the gel was completed liquefied, the resulting solution was still viscoelastic due to the nature of the collagen and peptides remaining in the solution.

The rheology data supports the anti-pruritic activity of α-amylase not being dependent on contamination by a protease.

Pruritus Reduction

Example 1

A male Caucasian septuagenarian applied bacterial α-amylase #6 solution to his skin damaged by pruritus, which resulted in inflamed red welts caused by scratching. The α-amylase solution was adjusted to pH 7 by NaOH, at a ratio of water/amylase of 99.66/0.34 by weight, wherein the α-amylase activity was 1 g/25,000 U. The solution was wiped onto inflamed, pruritic skin containing red welts using a non-woven cloth treated with the enzyme formulation. The solution was left on the skin for 10 minutes, with no observable discomfort, and removed by wiping several times with a wet cloth. The pruritus was reduced approximately 15 minutes after initial application, and the skin remained in a less inflamed state for at least 12 hours. The process was repeated every 12 hours for two days with elimination of pruritus and marked reduction and elimination of red welts.

Example 2

On another area of pruritic skin with irritation and inflammation, the above mentioned male utilized an antimicrobial amylase formulation based upon 25 mg of porcine pancreatic α-amylase #3 mixed in 21 g of PHMB-based Antimicrobial Composition (AC), prepared in 4 glass vials containing 5.0 ml amylase/AC per vial. Over a period of 48 hours, the content of each of the 4 vials were applied on a non-woven fabric every 12 hours to cleansed pruritic skin. Itching was abated during the first treatment, and irritation and inflammation greatly reduced after 48 hours.

Example 3

A 70 year old Caucasian female was bitten by mosquitoes over a two day period. The first area affected was untreated and resulted in a red, itchy bump of approximately one-quarter inch in diameter by day 2. On the second day, another mosquito bite occurred, becoming rapidly itchy. The second bite was as pruritic as the first bite and a powder of bacterial α-amylase #6 was applied directly to both affected areas (i.e., the first and second bites). The first bitten area had a decreased redness and decreased irritation after 15 minutes of treatment, whereas the second bitten area had decreased redness and elimination of pruritus with no red bump occurring.

Example 4

An Asian female developed a systemic pruritic urticaria. She applied bacterial α-amylase #6 solution to her skin. The α-amylase solution was adjusted to pH 7 by NaOH, at a ratio of water/amylase of 99.66/0.34 by weight, wherein the α-amylase activity was 1 g/25,000 U. The solution was wiped onto her right arm that was covered with pruritic hives using a paper towel with the enzyme formulation. The solution was left on the skin for 1 hour, with no observable discomfort, and removed by wiping several times with 3 wet paper towels. The pruritus was significantly reduced approximately 5 minutes after initial application, and lasted for at least 4 hours.

Amylase Compositions

Example 5

In Table 1, amylase formulations were prepared in water based upon α-amylase from animal, human, and bacterial sources, β-amylase from barley (a grain), and γ-amylase from fungi, and combinations thereof.

TABLE 1

Aqueous formulations of α-amylase, β-amylase, and γ-amylase.

| formulation | formulation ratio (wt %) | formulation (Units) |
|---|---|---|
| $H_2O$/α-amylase #1 | 99.2/0.8 | 1 g/250 U |
| $H_2O$/α-amylase #2 | 99.891/0.109 | 1 g/250 U |
| $H_2O$/α-amylase #3 | 99.88/0.12 | 1 g/250 U |
| $H_2O$/α-amylase #4 | 99.8/0.2 | 1 g/250 U |
| $H_2O$/α-amylase #5 | 99.95 g/0.05 | 1 g/250 U |
| $H_2O$/α-amylase #5 | 99.9/0.1 | 1 g/500 U |
| $H_2O$/α-amylase #6 | 99.9966/0.0033 | 1 g/250 U |
| $H_2O$/α-amylase #6 | 99.966/0.034 | 1 g/2,500 U |
| $H_2O$/α-amylase #6 | 96.6/3.4 | 1 g/250,000 U |
| $H_2O$/α-amylase #7 | 99.9803/0.0197 | 1 g/250 U |
| $H_2O$/α-amylase #7 | 99.803/0.197 | 1 g/2,500 U |
| $H_2O$/α-amylase #7 | 80.3/19.7 | 1 g/250,000 U |
| $H_2O$/β-amylase | 99.4/0.6 | 1 g/250 U |
| $H_2O$/β-amylase | 94/6 | 1 g/2500 U |
| $H_2O$/γ-amylase | 99.8/0.2 | 1 g/250 U |
| $H_2O$/γ-amylase #1 | 99/1 | 1 g/1,250 U |
| $H_2O$/γ-amylase #1 | 98/2 | 1 g/2,500 U |
| $H_2O$/γ-amylase #2 | 99.4/0.6 | 1 g/250 U |
| $H_2O$/α-amylase #6/β-amylase | 96.60/0.34/3.16 | 1 g/250 U/131 U |
| $H_2O$/α-amylase #6/β-amylase | 99.32/0.34/0.34 | 1 g/250 U/14 U |

Example 6

In Table 2, aqueous formulations of α-amylase with lipase are presented. This Example includes a combination of an amylolytic enzyme, α-amylase #3, and a lipolytic enzyme, lipase, wherein both enzymes are from porcine pancreas.

TABLE 2

Aqueous formulations of formulations of α-amylase #3 with lipase

| formulation | formulation ratio (wt %) | formulation (Units) |
|---|---|---|
| $H_2O$/α-amylase #3/lipase | 99.8/0.18/0.02 | 1 g/378 U/72 U |
| $H_2O$/α-amylase #3/lipase | 99.8/0.16/0.04 | 1 g/336 U/144 U |

Example 7

In Table 3 are presented various formulation of α-amylase #1 (from porcine pancreas) with the aqueous buffer DPBS, with the viscosity increasing hydrophilic neutral polymer hydroxypropylmethylcellulose (HPMC) and DPBS, with the cationic hydrophilic polymer Polymer-JR (cationic hydroxyethylcellulose) in water, with the keratolytic agent urea in water, with chlorophyllin in water, and with urea and chlorophyllin in water.

TABLE 3

Aqueous formulations of α-amylase

| formulation | formulation ratio (wt %) | formulation (Units) |
|---|---|---|
| DPBS/α-amylase #1 | 99.2/0.8 | 1 g/250 U |
| HPMC/DPBS/α-amylase #1 | 5.0/94.2 g/0.8 | 0.05 g/0.95 g/250 U |
| Polymer JR-30M/$H_2O$/α-amylase #1 | 5.0/94.2 g/0.8 | 0.05 g/0.95 g/250 U |
| $H_2O$/urea/α-amylase #1 | 89.2/10.0/0.8 | 1 g/250 U |
| $H_2O$/chlorophyllin/α-amylase #1 | 98.7/0.5/0.8 | 1 g/250 U |
| $H_2O$/chlorophyllin/α-amylase #1 | 98.2/1.0/0.8 | 1 g/250 U |
| $H_2O$/urea/chlorophyllin/α-amylase #1 | 88.7/10.0/0.5/0.8 | 1 g/250 U |

Example 8

In addition to water and buffered solutions (Tables 1 and 3), as well as α-amylase being utilized in powder form, the amylases can be mixed with several excipients, including hydrophobic hydrocarbons of petrolatum and mineral oil, hydrophilic —OH containing alcohols of glycerin and PEG 400, and the amphiphilic liquid PEG-12 Dimethicone (DC 193), a silicone polyether. In each case, α-amylase #1 (from porcine pancreas) could be dispersed in these excipients (Table 4). Other excipients could include various water-based buffers ranging in pH from 5.0-7.5, surfactants, silicones, polyether copolymers, polyoxyethylene ethers, vegetable and plant fats and oils, essential oils, hydrophilic and hydrophobic alcohols, vitamins, monoglycerides, laurate esters, myristate esters, palmitate esters, and stearate esters, preferably in liquid, gel, paste or slurry format.

TABLE 4

Excipients for α-amylase

| formulation | formulation ratio (wt %) | formulation (Units) |
|---|---|---|
| petrolatum/α-amylase #1 | 99.2/0.8 | 1 g/250 U |
| mineral oil/α-amylase #1 | 99.2/0.8 | 1 g/250 U |
| glycerin/α-amylase #1 | 99.2/0.8 | 1 g/250 U |
| PEG 400/α-amylase #1 | 99.2/0.8 | 1 g/250 U |
| DC 193/α-amylase #1 | 99.2/0.8 | 1 g/250 U |

Example 9

Because of the possibility of infection in pruritic tissue with irritation and/or inflammation, the addition of a biological agent that hinders or eradicates microorganisms is desired. Of particular interest are two antimicrobial biguanides used in wound care, poly(hexamethylene biguanide hydrochloride) (PHMB) and chlorhexidine digluconate (CHG). In Table 5 are compared three formulations of aqueous solutions of PHMB with α-amylase #6 and CHG with α-amylase #6, all at the same wt % of α-amylase #6 (from bacteria). For the PHMB-based solutions, the concentrations studied were at 0.50 wt % (500 ppm), 0.10 wt % (1,000 ppm) and 0.15 wt % (1,500 ppm), while that of CHG was 2.0 wt % (20,000 ppm). All solutions were compatible. Whereas PHMB and CHG can be utilized for their biocidal behavior, they can also be used as preservatives of amylase formulations.

TABLE 5

Antimicrobial formulations of α-amylase

| formulation | formulation ratio (wt %) | formulation (Units) |
|---|---|---|
| H₂O/PHMB/α-amylase #6 | 99.51/0.15/0.34 | 1 g/25,000 U |
| H₂O/PHMB/α-amylase #6 | 99.56/0.10/0.34 | 1 g/25,000 U |
| H₂O/PHMB/α-amylase #6 | 99.61/0.05/0.34 | 1 g/25,000 U |
| H₂O/CHG/α-amylase #6 | 97.66/2.00/0.34 | 1 g/25,000 U |

Example 10

Reverse microemulsions of α-amylase were also prepared based upon clear, homogeneous solutions of α-amylase in water solubilized by the reverse emulsion surfactant sodium bis(2-ethylhexyl)sulfosuccinate (AOT, Aerosol AOT) in the non-stinging, volatile solvent of hexamethyldisiloxane (HMDS) (Table 6). After solvent evaporation, α-amylase can be administered to pruritic tissue without necessitating wiping or rubbing and alleviating the occurrence of a burning or stinging response often associated with solvents on skin.

The formulations were prepared as follows: α-amylase #6 (from bacteria) was dissolved in water at a concentration of 0.17 wt % (solution A). AOT was dissolved in HMDS at a concentration of 50 wt % (solution B). 40 mg of solution A was mixed with 100 mg of solution B, and the cloudy solution was shaken until clarity resulted. To this mixture was then added 860 mg of HMDS, forming a reverse microemulsion wherein solution clarity was maintained.

TABLE 6

| Reverse microemulsions of α-amylase with AOT in HMDS/water | | | |
|---|---|---|---|
| formulation | formulation ratio (wt %) | formulation (Units) | appearance |
| HMDS/AOT/$H_2O$/ α-amylase #6 | 91.0/5.0/4.0/0.0068 | 1 g/500 | clear |
| HMDS/AOT/$H_2O$/ α-amylase #6 | 99.1/0.5/0.4/0.00068 | 1 g/50 | clear |

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

The invention claimed is:

1. A method of ameliorating a sensation of itching, the method comprising:

topically administering a therapeutically effective amount of an enzymatic pruritic composition to itching tissue, wherein said enzymatic pruritic composition comprises:

0.10 to 99.5% by weight of an amylase component, wherein the amylase component comprises an amylase selected from the group consisting of non-human animal amylase, bacteria amylase, plant amylase, fungi amylase, and recombinant amylase, and at least one pharmaceutically or cosmetically acceptable carrier or excipient in an amount of up to 99.9% by weight, wherein the percentages are based on a total weight of the enzymatic pruritic composition, wherein, if a proteolytic enzyme component is present in the enzymatic pruritic composition, then the amylase component and proteolytic enzyme component are present in a weight ratio of at least 10:1; and wherein the itching tissue is selected from the group consisting of rashes, dry skin, pimples, contact dermatitis, psoriasis, rosacea, seborrheic dermatitis, insect bites, acne, cysts, blisters, chemical irritants, biological irritants, sunburn, and frostbite.

2. The method according claim 1, wherein said amylase component is a bacterial or fungal amylase selected from the group consisting of *Bacillus* spp. and *Aspergillus* spp.

3. The method according to claim 1, wherein said amylase component comprises at least 10% by weight of α-amylase.

4. The method according to claim 3, wherein said amylase component comprises β-amylase, γ-amylase, or both.

5. The method according to claim 1, wherein said enzymatic pruritic composition further comprises up to 20% by weight of a hydrolytic enzyme component selected from the group consisting of chondroitinases, hyaluronidases, lipases, glycosidases, heparanases, dermatanases, pullulanases, N-acetylglucosaminidase, lactases, phospholipases, transglycosylases, esterases, thioester hydrolyases, sulfatases, escharases, nucleases, phosphatases, phosphodiesterases, mannanases, mannosidases, isoamylases, lyases, inulinases, keratinases, tannases, pentosanases, glucanases, arabinosidases, pectinases, cellulases, chitinases, xylanases, cutinases, pectate lyases, hemicellulases, and combinations thereof, wherein the percentage is based on the total weight of the amylase component and the hydrolytic enzyme component.

6. The method according to claim 1, wherein the amylase component comprises α-amylase selected from the group consisting of human pancreas amylase, animal pancreas amylase, and bacteria amylase.

7. The method according to claim 1, wherein said enzymatic pruritic composition further comprises up to 20% by weight of other enzymes selected from the group consisting of oxidases, peroxidases, glucose oxidases, catalases, oxidoreductases, phenoloxidases, laccases, lipoxygenases, isomerases, and ligninases, wherein the percentage is based on the total weight of the amylase component and the other enzymes.

8. The method according to claim 1, wherein said enzymatic pruritic composition further comprises at least one polymeric biguanide in an amount of at least 0.01 weight percent to 1.0 weight percent based on the total weight of the enzymatic pruritic composition.

9. The method according to claim 8, wherein said polymeric biguanide comprises poly(hexamethylene biguanide) or one of its salts.

10. The method according to claim 1, wherein said enzymatic pruritic composition further comprises a water-soluble polymer at a concentration of from 0.01 weight % to 50 weight % of the composition, wherein the water-soluble polymer is selected from the group consisting of methylcellulose, hydroxyethylcellulose, hydroxypropylcellulose, hydroxypropylmethylcellulose, carboxymethylcellulose, guar gum, hydroxyethylguar, hydroxypropylguar, hydroxypropylmethylguar, carboxymethylguar, carboxymethylchitosan, locust bean gum, carrageenan, xanthan gum, gellan gum, Aloe vera gel, scleroglucan, schizophyllan, gum arabic, tamarind gum, poly(vinyl alcohol), poly(ethylene oxide), poly(ethylene glycol), poly(methyl vinyl ether), Carbomer and its salts, poly(acrylic acid) and its salts, poly(methacrylic acid) and its salts, sodium poly(2-acrylamido-2-methylpropanesulfonate), polyacrylamide, poly(N,N- dimethylacrylamide), poly(N-vinylacetamide), poly(N-vinylformamide), poly(2-hydroxyethyl methacrylate), poly(glyceryl methacrylate), poly(N-vinylpyrrolidone), poly(N-isopropylacrylamide) and poly(N-vinylcaprolactam), and combinations thereof.

11. The method according to claim 1, wherein said enzymatic pruritic composition further comprises a chelating agent at a concentration of from 0.01 weight % to 1 weight % based on a total weight of the composition, wherein said chelating agent is selected from the group consisting of ethylenediaminetetraacetic acid (EDTA), nitrilotriacetic acid, nitrilotripropionic acid, diethylenetriaminepentaacetic acid, 2-hydroxyethylethylenediaminetriacetic acid, 1,6-diaminohexamethylenetetraacetic acid, 1,2-diaminocyclohexanetetraacetic acid, O,O'-bis(2-aminoethyl)ethyleneglycoltetraacetic acid, 1,3-diaminopropanetetraacetic acid, N,N'-bis(2-hydroxybenzyl)ethylenediamine-N,N'-diacetic acid, ethylenediamine-N,N'-diacetic acid, ethylenediamine-N,N'-dipropionic acid, triethylenetetraaminehexaacetic acid, ethylenediamine-N,N'-bis(methylenephosphonic acid), iminodiacetic acid, monosodium-N-lauryl-R-iminodipropionic acid (sodium lauriminodipropionate), N,N-bis(2-hydroxyethyl)glycine, 1,3-diamino-2-hydroxypropanetetraacetic acid, 1,2-diaminopropanetetraacetic acid, ethylenediaminetetrakis(methylenephosphonic acid), N-(2-hydroxyethyl)iminodiacetic acid, biphosphonates, editronate, salts thereof, and combinations thereof.

12. The method according to claim 1, wherein said enzymatic pruritic composition further comprises a monoalkyl glycol selected from the group consisting of 1,2-propanediol (propylene glycol), 1,2-butanediol, 1,2-pentanediol, 1,2-hexanediol, 1,2-heptanediol, 1,2-octanediol (caprylyl glycol), 1,2-nonanediol, 1,2-decanediol, 1,2-undecanediol, 1,2-dodecanediol, 1,2-tridecanediol, 1,2-tetradecanediol, 1,2-pentadecanediol, 1,2-hexadecanediol, 1,2-heptadecanediol, 1,2-octadecanediol, 2-methyl-2,4-pentanediol, 1,3-butanediol, diethylene glycol, triethylene glycol, glycol bis(hydroxyethyl) ether, and combinations thereof.

13. The method according to claim 1, wherein said enzymatic pruritic composition further comprises a glycerol alkyl ether selected from the group consisting of 1-O-heptylglycerol, 1-O-octylglycerol, 1-O-nonylglycerol, 1-O-decylglycerol, 1-O-undecylglycerol, 1-O-dodecylglycerol, 1-O-tridecylglycerol, 1-O-tetradecylglycerol, 1-O-pentadecylglycerol, 1-O-hexadecylglycerol (chimyl alcohol), 1-O-heptadecylglycerol, 1-O-octadecylglycerol (batyl alcohol), 1-O-octadec-9-enyl glycerol, selachyl alcohol, glycerol 1-(2-ethylhexyl) ether, octoxyglycerin, 2-ethylhexyl glycerin, 3-(2-ethylhexyloxy)propane-1,2-diol, glycerol 1-heptyl ether, glycerol 1-octyl ether, glycerol 1-decyl ether, glycerol 1-dodecyl ether, glycerol 1-tridecyl ether, glycerol 1-tetradecyl ether, glycerol 1-pentadecyl ether, glycerol 1-hexadecyl ether, glycerol 1-octadecyl ether, and combinations thereof.

14. The method according to claim 1, wherein said enzymatic pruritic composition further comprises:
at least one polymeric biguanide in an amount of at least 0.01 weight %, and
a vicinal diol component, comprising a vicinal diol selected from the group consisting of a monoalkyl glycol, a monoalkyl glycerol, and a combination thereof, at a concentration of 0.05 weight % to 4 weight %, wherein the percentages of polymeric biguanide and vicinal diol are based on a total weight of the enzymatic pruritic composition.

15. The method according to claim 1, wherein said enzymatic pruritic composition further comprises a medicament selected from the group consisting of analgesic agents, anesthetic agents, neuropathic pain agents, lidocaine, capsaicin, calamine lotion, benzocaine, tetracaine, prilocaine, bupivacaine, levobupivacaine, procaine, carbocaine, etidocaine, mepivacaine, nortripylene, amitriptyline, pregabalin, diclofenac, fentanyl, gabapentin, opioids, ketoconazole, non-steroidal anti-inflammatory agents, salicylates, leukotriene antagonists, and combinations thereof.

16. The method according to claim 15, wherein the at least one medicament is selected from the group consisting of lidocaine, capsaicin, calamine lotion, benzocaine, tetracaine, prilocaine, bupivacaine, levobupivacaine, procaine, carbocaine, etidocaine, mepivacaine, nortripylene, amitriptyline, pregabalin, diclofenac, fentanyl, gabapentin, ketoconazole, opioids, non-steroidal anti-inflammatory agents, salicylates, and mixtures thereof.

17. The method according to claim 1, wherein the enzymatic pruritic composition is in a form selected from the group consisting of a powder, an aqueous solution, an organic liquid solution, a silicone fluid, a gel, a hydrogel, a cream, a film, a latex, an aerosol, a slurry, a paste, a balm, an ointment, and a foam.

18. The method according to claim 1, wherein said amylase component is adsorbed on or in a natural or synthetic fiber, mesh, gauze, cloth, hydrocolloid, alginate, hydrogel, semipermeable film, permeable film, or a natural or synthetic polymer.

19. The method according to claim 1, wherein said enzymatic pruritic composition further comprises a buffering agent.

20. The method according to claim 1, wherein said enzymatic pruritic composition further comprises a reverse microemulsion comprising α-amylase solubilized by a hydrophobic reverse emulsion surfactant in a non-stinging, volatile, hydrophobic solvent, wherein said non-stinging, volatile, hydrophobic solvent is selected from the group consisting of volatile linear and cyclic siloxanes, volatile alkanes, volatile fluorocarbons and chlorofluorocarbons, liquid carbon dioxide under pressure, and combinations thereof.

21. The method according to claim 1, wherein the proteolytic enzyme component is present.

* * * * *